(12) United States Patent
Stone et al.

(10) Patent No.: US 9,724,245 B2
(45) Date of Patent: Aug. 8, 2017

(54) FORMED WEB COMPRISING CHADS

(75) Inventors: Keith Joseph Stone, Fairfield, OH (US); Richard George Coe, Cincinnati, OH (US); Mathias Johannes Hilpert, Mason, OH (US); James William Busch, Maineville, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1094 days.

(21) Appl. No.: 13/094,593

(22) Filed: Apr. 26, 2011

(65) Prior Publication Data

US 2012/0277701 A1 Nov. 1, 2012

(51) Int. Cl.
| | |
|---|---|
| B32B 3/24 | (2006.01) |
| B32B 3/30 | (2006.01) |
| A61F 13/15 | (2006.01) |
| A61F 13/511 | (2006.01) |
| A61F 13/512 | (2006.01) |
| A61F 13/514 | (2006.01) |
| A61F 13/513 | (2006.01) |
| B32B 7/04 | (2006.01) |
| B32B 3/26 | (2006.01) |
| A61F 13/51 | (2006.01) |

(52) U.S. Cl.
CPC ...... *A61F 13/15731* (2013.01); *A61F 13/512* (2013.01); *A61F 13/5121* (2013.01); *A61F 13/51476* (2013.01); *A61F 13/51* (2013.01); *A61F 13/513* (2013.01); *A61F 13/51104* (2013.01); *A61F 2013/51344* (2013.01); *A61F 2013/51383* (2013.01); *B32B 3/266* (2013.01); *B32B 3/30* (2013.01); *B32B 7/04* (2013.01); *B32B 2555/02* (2013.01); *Y10T 428/24182* (2015.01); *Y10T 428/24281* (2015.01)

(58) Field of Classification Search
None
See application file for complete search history.

(56) References Cited

U.S. PATENT DOCUMENTS

| 2,068,456 A | 1/1937 | Hooper | |
|---|---|---|---|
| 2,130,375 A * | 9/1938 | Atkins | A47K 10/16 162/114 |

(Continued)

FOREIGN PATENT DOCUMENTS

| CN | 2912578 Y * | 6/2007 |
|---|---|---|
| DE | 34 39 555 A1 | 4/1986 |

(Continued)

OTHER PUBLICATIONS

Machine Translation of JP 2003126143 A, May 2003.*

(Continued)

*Primary Examiner* — Jeff Vonch
(74) *Attorney, Agent, or Firm* — George H. Leal; Megan C. Hymore

(57) ABSTRACT

A formed web comprising discrete three-dimensional elements formed therein, wherein at least some of the discrete three-dimensional elements comprise chads with corresponding apertures, wherein the aperture has a perimeter, wherein the chad has a length, wherein the chads are attached along a portion of the aperture perimeter which forms a connection segment, wherein the connection segment is less than about 50% of the entire aperture perimeter, and wherein the web comprises a film.

21 Claims, 22 Drawing Sheets

(56) References Cited

U.S. PATENT DOCUMENTS

| | | | |
|---|---|---|---|
| 2,275,425 A | 3/1942 | Grabec | |
| 2,404,758 A | 7/1946 | Teague et al. | |
| 2,633,441 A | 3/1953 | Buttress | |
| 2,748,863 A | 6/1956 | Benton | |
| 2,924,863 A | 2/1960 | Chavannes | |
| 3,073,304 A | 1/1963 | Schaar | |
| 3,081,500 A | 3/1963 | Griswold et al. | |
| 3,081,512 A | 3/1963 | Griswold | |
| 3,085,608 A * | 4/1963 | Mathues | B26F 1/24 206/439 |
| 3,137,893 A | 6/1964 | Gelpke | |
| 3,355,974 A | 12/1967 | Carmichael | |
| 3,399,822 A * | 9/1968 | Kugler | B65D 33/01 383/103 |
| 3,496,259 A | 2/1970 | Guenther | |
| 3,509,007 A * | 4/1970 | Kalwaites | 428/132 |
| 3,511,740 A | 5/1970 | Sanders | |
| 3,542,634 A | 11/1970 | Such et al. | |
| 3,566,726 A | 3/1971 | Politis | |
| 3,579,763 A | 5/1971 | Sommer | |
| 3,594,261 A * | 7/1971 | Broerman | D04H 13/00 156/252 |
| 3,681,182 A | 8/1972 | Kalwaites | |
| 3,681,183 A | 8/1972 | Kalwaites | |
| 3,684,284 A | 8/1972 | Tranfield | |
| 3,695,270 A | 10/1972 | Dostal | |
| 3,718,059 A | 2/1973 | Clayton | |
| 3,719,736 A | 3/1973 | Woodruff | |
| 3,760,671 A | 9/1973 | Jenkins | |
| 3,779,285 A | 12/1973 | Sinibaldo | |
| 3,881,987 A | 5/1975 | Benz | |
| 3,911,187 A | 10/1975 | Raley | |
| 3,949,127 A | 4/1976 | Ostermeier et al. | |
| 3,965,906 A | 6/1976 | Karami | |
| 4,035,881 A | 7/1977 | Zocher | |
| 4,042,453 A | 8/1977 | Conway et al. | |
| 4,135,021 A | 1/1979 | Patchell et al. | |
| 4,211,743 A | 7/1980 | Kos et al. | |
| 4,276,336 A | 6/1981 | Sabee | |
| 4,319,868 A | 3/1982 | Riemersma et al. | |
| 4,343,848 A | 8/1982 | Leonard, Jr. | |
| 4,377,544 A * | 3/1983 | Rasmussen | B26F 1/26 264/139 |
| 4,379,799 A | 4/1983 | Holmes et al. | |
| 4,397,644 A | 8/1983 | Matthews et al. | |
| 4,463,045 A | 7/1984 | Ahr et al. | |
| 4,465,726 A | 8/1984 | Holmes et al. | |
| 4,469,734 A | 9/1984 | Minto et al. | |
| 4,546,029 A | 10/1985 | Cancio et al. | |
| 4,588,630 A | 5/1986 | Shimalla | |
| 4,626,254 A * | 12/1986 | Widlund et al. | 604/383 |
| 4,629,643 A * | 12/1986 | Curro | A61F 13/5146 428/131 |
| 4,636,417 A * | 1/1987 | Rasmussen | B26F 1/26 428/131 |
| 4,645,500 A * | 2/1987 | Steer | 604/378 |
| 4,695,422 A | 9/1987 | Curro et al. | |
| 4,741,941 A | 5/1988 | Englebert et al. | |
| 4,758,297 A | 7/1988 | Calligarich | |
| 4,772,444 A * | 9/1988 | Curro | A61F 13/5146 264/154 |
| 4,778,644 A | 10/1988 | Curro et al. | |
| 4,781,962 A | 11/1988 | Zamarripa et al. | |
| 4,798,604 A | 1/1989 | Carter | |
| 4,820,294 A | 4/1989 | Morris | |
| 4,840,829 A | 6/1989 | Suzuki et al. | |
| 4,859,519 A | 8/1989 | Cabe, Jr. et al. | |
| 4,886,632 A | 12/1989 | Van Iten et al. | |
| 4,895,749 A * | 1/1990 | Rose | B26F 1/26 264/504 |
| 4,921,034 A | 5/1990 | Burgess et al. | |
| 4,935,087 A | 6/1990 | Gilman | |
| 4,953,270 A | 9/1990 | Gilpatrick | |
| 5,019,062 A | 5/1991 | Ryan et al. | |
| 5,062,418 A | 11/1991 | Dyer et al. | |
| 5,144,730 A | 9/1992 | Dilo | |
| 5,158,819 A | 10/1992 | Goodman et al. | |
| 5,165,979 A | 11/1992 | Watkins et al. | |
| 5,171,238 A | 12/1992 | Kajander | |
| 5,180,620 A | 1/1993 | Mende | |
| 5,188,625 A | 2/1993 | Van Iten et al. | |
| 5,223,319 A | 6/1993 | Cotton et al. | |
| 5,242,632 A | 9/1993 | Mende | |
| 5,281,371 A | 1/1994 | Tamura et al. | |
| 5,324,279 A * | 6/1994 | Lancaster | A44B 18/0053 24/306 |
| 5,382,245 A | 1/1995 | Thompson et al. | |
| 5,383,870 A | 1/1995 | Takai et al. | |
| 5,387,209 A | 2/1995 | Yamamoto et al. | |
| 5,414,914 A | 5/1995 | Suzuki et al. | |
| 5,415,640 A | 5/1995 | Kirby et al. | |
| 5,429,854 A | 7/1995 | Currie et al. | |
| 5,437,653 A | 8/1995 | Gilman et al. | |
| 5,470,326 A | 11/1995 | Dabi et al. | |
| 5,508,080 A | 4/1996 | Sorimachi et al. | |
| 5,518,801 A | 5/1996 | Chappell et al. | |
| 5,533,991 A | 7/1996 | Kirby et al. | |
| 5,536,555 A * | 7/1996 | Zelazoski et al. | 428/138 |
| 5,554,145 A | 9/1996 | Roe et al. | |
| 5,560,794 A | 10/1996 | Currie et al. | |
| 5,565,255 A * | 10/1996 | Young | A61F 13/51403 427/358 |
| 5,567,501 A | 10/1996 | Srinivasan et al. | |
| 5,573,719 A | 11/1996 | Fitting | |
| 5,575,874 A | 11/1996 | Griesbach, III et al. | |
| 5,580,418 A | 12/1996 | Alikhan | |
| 5,599,420 A | 2/1997 | Yeo et al. | |
| 5,624,427 A | 4/1997 | Bergman et al. | |
| 5,626,571 A | 5/1997 | Young et al. | |
| 5,628,097 A | 5/1997 | Benson et al. | |
| 5,648,142 A * | 7/1997 | Phillips | A61F 13/512 428/131 |
| 5,650,215 A | 7/1997 | Mazurek et al. | |
| 5,656,119 A | 8/1997 | Srinivasan et al. | |
| 5,658,639 A | 8/1997 | Curro et al. | |
| 5,667,619 A | 9/1997 | Alikhan | |
| 5,667,625 A | 9/1997 | Alikhan | |
| 5,670,110 A | 9/1997 | Dirk et al. | |
| 5,691,035 A | 11/1997 | Chappell et al. | |
| 5,700,255 A | 12/1997 | Curro et al. | |
| 5,704,101 A | 1/1998 | Majors et al. | |
| 5,709,829 A | 1/1998 | Giacometti | |
| 5,714,107 A | 2/1998 | Levy et al. | |
| 5,723,087 A | 3/1998 | Chappell et al. | |
| 5,743,776 A | 4/1998 | Igaue et al. | |
| 5,804,021 A | 9/1998 | Abuto et al. | |
| 5,814,389 A | 9/1998 | Giacometti | |
| 5,817,394 A | 10/1998 | Alikhan et al. | |
| 5,824,352 A * | 10/1998 | Yang | A61F 13/15707 264/504 |
| 5,841,107 A | 11/1998 | Riva | |
| 5,858,504 A | 1/1999 | Fitting | |
| 5,858,515 A | 1/1999 | Stokes et al. | |
| 5,879,494 A | 3/1999 | Hoff et al. | |
| 5,891,544 A | 4/1999 | Chappell et al. | |
| 5,895,623 A | 4/1999 | Trokhan et al. | |
| 5,914,084 A | 6/1999 | Benson et al. | |
| 5,916,661 A | 6/1999 | Benson et al. | |
| 5,919,177 A | 7/1999 | Georger et al. | |
| 5,925,026 A | 7/1999 | Arteman et al. | |
| 5,945,196 A | 8/1999 | Rieker et al. | |
| 5,964,742 A | 10/1999 | McCormack et al. | |
| 5,968,029 A | 10/1999 | Chappell et al. | |
| 5,986,167 A | 11/1999 | Arteman et al. | |
| 5,993,432 A | 11/1999 | Lodge et al. | |
| 6,007,468 A | 12/1999 | Giacometti | |
| 6,025,050 A | 2/2000 | Srinivasan et al. | |
| 6,027,483 A | 2/2000 | Chappell et al. | |
| 6,039,555 A | 3/2000 | Tsuji et al. | |
| 6,080,276 A | 6/2000 | Burgess | |
| 6,096,016 A | 8/2000 | Tsuji et al. | |
| 6,114,263 A | 9/2000 | Benson et al. | |
| 6,117,524 A * | 9/2000 | Hisanaka et al. | 428/137 |

(56) References Cited

U.S. PATENT DOCUMENTS

| | | | |
|---|---|---|---|
| 6,120,718 A | 9/2000 | Kotek et al. |
| 6,129,801 A | 10/2000 | Benson et al. |
| H1927 H | 12/2000 | Chen et al. |
| 6,155,083 A | 12/2000 | Goeser et al. |
| 6,168,849 B1 | 1/2001 | Braverman et al. |
| 6,176,954 B1 | 1/2001 | Tsuji et al. |
| 6,247,914 B1 | 6/2001 | Lindquist et al. |
| D444,631 S | 7/2001 | Woodbridge et al. |
| 6,264,872 B1 | 7/2001 | Majors et al. |
| 6,287,407 B1 | 9/2001 | Stein et al. |
| 6,383,431 B1 | 5/2002 | Dobrin et al. |
| 6,395,122 B1 | 5/2002 | Hisanaka et al. |
| 6,395,211 B1 | 5/2002 | Dettmer et al. |
| 6,398,895 B1 | 6/2002 | Stein et al. |
| 6,410,823 B1* | 6/2002 | Daley .................. A61F 13/512 604/383 |
| 6,420,625 B1 | 7/2002 | Jones et al. |
| 6,423,884 B1 | 7/2002 | Oehmen |
| 6,451,718 B1 | 9/2002 | Yamada et al. |
| 6,452,064 B1 | 9/2002 | Thoren et al. |
| 6,458,447 B1 | 10/2002 | Cabell et al. |
| 6,468,626 B1* | 10/2002 | Takai .................. A61F 13/512 428/131 |
| 6,479,130 B1 | 11/2002 | Takai et al. |
| D466,702 S | 12/2002 | Carlson et al. |
| 6,506,329 B1 | 1/2003 | Curro et al. |
| 6,537,936 B1 | 3/2003 | Busam et al. |
| 6,599,612 B1* | 7/2003 | Gray .................. A61F 13/512 428/131 |
| 6,620,485 B1 | 9/2003 | Benson et al. |
| 6,632,504 B1 | 10/2003 | Gillespie et al. |
| D481,872 S | 11/2003 | Hennel et al. |
| 6,647,549 B2 | 11/2003 | McDevitt et al. |
| 6,669,878 B2 | 12/2003 | Yamada et al. |
| 6,716,498 B2 | 4/2004 | Curro et al. |
| 6,719,742 B1 | 4/2004 | McCormack et al. |
| 6,726,870 B1 | 4/2004 | Benson et al. |
| 6,736,916 B2 | 5/2004 | Steinke et al. |
| 6,739,024 B1 | 5/2004 | Wagner |
| 6,794,626 B2 | 9/2004 | Kiermeier et al. |
| 6,808,791 B2 | 10/2004 | Curro et al. |
| 6,818,802 B2 | 11/2004 | Takai et al. |
| 6,830,800 B2 | 12/2004 | Curro et al. |
| 6,837,956 B2 | 1/2005 | Cowell et al. |
| 6,846,172 B2 | 1/2005 | Vaughn et al. |
| 6,846,445 B2 | 1/2005 | Kim et al. |
| 6,855,220 B2 | 2/2005 | Wildeman |
| 6,863,960 B2 | 3/2005 | Curro et al. |
| 6,872,274 B2 | 3/2005 | Kauschke et al. |
| 6,884,494 B1 | 4/2005 | Curro et al. |
| 6,946,182 B1* | 9/2005 | Allgeuer .................. B29C 43/222 264/134 |
| 6,989,187 B2* | 1/2006 | Thomas .................. A61F 13/512 428/131 |
| 7,005,558 B1 | 2/2006 | Johansson et al. |
| 7,037,569 B2 | 5/2006 | Curro et al. |
| 7,297,226 B2 | 11/2007 | Schulz |
| 7,402,723 B2 | 7/2008 | Stone et al. |
| 7,521,588 B2 | 4/2009 | Stone et al. |
| 7,642,207 B2 | 1/2010 | Boehmer et al. |
| 7,655,176 B2 | 2/2010 | Stone et al. |
| 7,799,254 B2 | 9/2010 | Harvey et al. |
| 2001/0005540 A1* | 6/2001 | Hisanaka .................. A61F 13/512 428/131 |
| 2001/0014796 A1 | 8/2001 | Mizutani et al. |
| 2002/0026169 A1* | 2/2002 | Takai .................. A61F 13/512 604/378 |
| 2002/0039867 A1 | 4/2002 | Curro et al. |
| 2002/0103469 A1 | 8/2002 | Chen et al. |
| 2002/0105110 A1 | 8/2002 | Dobrin et al. |
| 2002/0107495 A1 | 8/2002 | Chen et al. |
| 2002/0119720 A1 | 8/2002 | Arora et al. |
| 2002/0132544 A1 | 9/2002 | Takagaki |
| 2003/0003269 A1* | 1/2003 | Lee .................. A61F 13/15203 428/131 |
| 2003/0021951 A1 | 1/2003 | Desai et al. |
| 2003/0028165 A1 | 2/2003 | Curro et al. |
| 2003/0085213 A1 | 5/2003 | Burckhardt et al. |
| 2003/0187170 A1 | 10/2003 | Burmeister |
| 2003/0191442 A1 | 10/2003 | Bewick-Sonntag et al. |
| 2003/0191443 A1 | 10/2003 | Taylor et al. |
| 2003/0201582 A1 | 10/2003 | Gray |
| 2003/0228445 A1 | 12/2003 | Vaughn et al. |
| 2004/0046290 A1 | 3/2004 | Kim et al. |
| 2004/0121686 A1 | 6/2004 | Wong et al. |
| 2004/0122395 A1 | 6/2004 | Stone et al. |
| 2004/0122396 A1 | 6/2004 | Maldonado et al. |
| 2004/0126531 A1 | 7/2004 | Harvey et al. |
| 2004/0131820 A1 | 7/2004 | Turner et al. |
| 2004/0137200 A1 | 7/2004 | Chhabra et al. |
| 2004/0157036 A1 | 8/2004 | Provost et al. |
| 2004/0161586 A1 | 8/2004 | Cree et al. |
| 2004/0209041 A1 | 10/2004 | Muth et al. |
| 2004/0229008 A1 | 11/2004 | Hoying et al. |
| 2004/0242097 A1 | 12/2004 | Hasenoehrl et al. |
| 2004/0265533 A1 | 12/2004 | Hoying et al. |
| 2004/0265534 A1 | 12/2004 | Curro et al. |
| 2005/0019526 A1* | 1/2005 | Mizutani .................. A61F 13/512 428/131 |
| 2005/0064136 A1* | 3/2005 | Turner et al. .................. 428/131 |
| 2005/0096614 A1 | 5/2005 | Perez et al. |
| 2005/0123726 A1 | 6/2005 | Broering et al. |
| 2005/0191496 A1 | 9/2005 | Gray et al. |
| 2005/0279470 A1 | 12/2005 | Redd et al. |
| 2006/0019056 A1 | 1/2006 | Turner et al. |
| 2006/0087053 A1 | 4/2006 | O'Donnell et al. |
| 2006/0286343 A1 | 12/2006 | Curro et al. |
| 2007/0029694 A1 | 2/2007 | Cree et al. |
| 2007/0062658 A1 | 3/2007 | Wiwi et al. |
| 2007/0144693 A1 | 6/2007 | Ruthven et al. |
| 2007/0261224 A1 | 11/2007 | McLeod |
| 2008/0138574 A1* | 6/2008 | Maschino .................. A61F 13/512 428/137 |
| 2008/0200320 A1 | 8/2008 | Buckner et al. |
| 2008/0224351 A1 | 9/2008 | Curro et al. |
| 2008/0264275 A1 | 10/2008 | Wilhelm et al. |
| 2009/0026651 A1* | 1/2009 | Lee et al. .................. 264/156 |
| 2009/0302504 A1* | 12/2009 | Di Berardino .................. B26D 7/1863 264/413 |
| 2010/0036346 A1* | 2/2010 | Hammons et al. .................. 604/378 |
| 2010/0102488 A1 | 4/2010 | Stone et al. |
| 2010/0201024 A1 | 8/2010 | Gibson |
| 2010/0230857 A1 | 9/2010 | Muhs et al. |
| 2010/0230858 A1 | 9/2010 | Stone et al. |
| 2010/0230866 A1 | 9/2010 | Gray et al. |
| 2010/0230867 A1 | 9/2010 | Gray et al. |
| 2010/0233428 A1 | 9/2010 | Stone et al. |
| 2010/0233438 A1 | 9/2010 | Stone et al. |
| 2010/0233439 A1 | 9/2010 | Stone et al. |
| 2010/0247844 A1 | 9/2010 | Curro et al. |
| 2010/0255258 A1 | 10/2010 | Curro et al. |
| 2012/0064280 A1 | 3/2012 | Hammons et al. |
| 2012/0064298 A1 | 3/2012 | Orr et al. |
| 2012/0273146 A1 | 11/2012 | Curro et al. |
| 2012/0273148 A1 | 11/2012 | Orr et al. |
| 2012/0273990 A1 | 11/2012 | O'Donnell et al. |
| 2012/0276238 A1 | 11/2012 | Strube et al. |
| 2012/0276341 A1 | 11/2012 | Lake et al. |
| 2012/0276637 A1 | 11/2012 | Zhou et al. |
| 2012/0277393 A1 | 11/2012 | Curro et al. |
| 2012/0277704 A1 | 11/2012 | Marinelli et al. |
| 2012/0277705 A1 | 11/2012 | Marinelli et al. |
| 2012/0277706 A1 | 11/2012 | Marinelli et al. |
| 2012/0277707 A1 | 11/2012 | Orr et al. |
| 2012/0277708 A1 | 11/2012 | Marinelli et al. |
| 2012/0277709 A1 | 11/2012 | Marinelli et al. |
| 2012/0277710 A1 | 11/2012 | Marinelli et al. |
| 2012/0295060 A1 | 11/2012 | Mullane |

(56) References Cited

U.S. PATENT DOCUMENTS

FOREIGN PATENT DOCUMENTS

| EP | 403187 A1 | * | 12/1990 | | |
|---|---|---|---|---|---|
| EP | 509012 | | 10/1992 | | |
| EP | 0 598 970 | | 6/1994 | | |
| EP | 598970 A1 | | 6/1994 | | |
| EP | 955159 A1 | | 11/1999 | | |
| EP | 963747 A1 | | 12/1999 | | |
| EP | 1004412 A1 | | 5/2000 | | |
| GB | 900083 A | | 7/1962 | | |
| GB | 1344054 A | | 1/1974 | | |
| GB | 2333683 A | * | 8/1999 | ............... | A01G 9/22 |
| GB | 2333724 A | * | 8/1999 | ............. | A41D 31/00 |
| JP | 2003126143 A | * | 5/2003 | ............. | A61F 13/49 |
| WO | 9515138 A1 | | 6/1995 | | |
| WO | WO 97/13633 A1 | | 4/1997 | | |
| WO | WO 0059438 A1 | * | 10/2000 | ........... | A61F 13/512 |
| WO | WO 01/08869 A1 | | 2/2001 | | |
| WO | 02100632 A1 | | 12/2002 | | |
| WO | 2005011936 A1 | | 2/2005 | | |
| WO | WO 2008/120959 A1 | | 10/2008 | | |

OTHER PUBLICATIONS

International Search Report dated Oct. 5, 2012, 9 pages.
U.S. Appl. No. 12/879,531, filed Sep. 10, 2010, Keith Joseph Stone.
U.S. Appl. No. 12/879,567, filed Sep. 10, 2010, Sara Beth Gross.
U.S. Appl. No. 12/879,531, Process for Making a Film/Nonwoven Laminate.
U.S. Appl. No. 12/879,567, Process for Making an Embossed Web.
PCT International Search Report, mailed Apr. 12, 2006, 6 pages.
Nagarajan, Abbott, Yao; Rubber-Assisted Embossing Process; School of Polymer, Textile & Fiber Eng., Georgia Institute of Technology, Atlanta, GA 30332; ANTEC (2007) vol. 5, pp. 2921-2925, 5 pages.
Chang, Yang; Gas pressurized hot embossing for transcription of micro-features; Microsystem Technologies (2003) vol. 10, pp. 76-80, 5 pages; Springer-Verlag.
Dreuth, Heiden; Thermoplastic structuring of thin polymer films; Sensors and Actuators (1999) vol. 78, pp. 198-204, 7 pages; Institute of Applied Physics, University of Giessen, Heinrich-Buff-Ring 16 D-35392 Giessen, Germany; Elsevier Science S.A.
Heckele, Schomburg; Review on micro molding of thermoplastic polymers; Institute of Physics Publishing; Journal of Micromechanics and Microengineering (2004) vol. 14, No. 3, pp. R1-R14, 14 pages; IOP Publishing Ltd.
Kimerling, Liu, Kim, Yao; Rapid hot embossing of polymer microfeatures; Microsystem Technologies (2006) vol. 12, No. 8, pp. 730-735, 6 pages; School of Polymer, Textile and Fiber Eng., Georgia Institute of Technology, Atlanta GA 30332.
Nagarajan, Yao, Ellis, Azadegan; Through-Thickness Embossing Process for Fabrication of Three-Dimensional Thermoplastic Parts; School of Polymer, Textile & Fiber Eng., Georgia Institute of Technology, Atlanta GA 30332 and Delphi Research Labs, Shelby Township, Michigan 48315; Polymer Engineering and Science (2007) vol. 47, No. 12, pp. 2075-2084, 10 pages.
Rowland, King; Polymer deformation and filling modes during microembossing; Woodruff School of Mechanical Engineering, Georgia Institute of Technology, Atlanta, GA 30329-0405; Institute of Physics Publishing; Journal of Micromechanics and Microengineering (2004) vol. 14, No. 12, pp. 1625-1632, 8 pages; IOP Publishing Ltd.
Truckenmuller, Giselbrecht; Microthermoforming of flexible, not-buried hollow microstructures for chip-based life sciences applications; IEE Proceedings—Nanobiotechnology (Aug. 2004) vol. 151, No. 4, pp. 163-166; 4 pages.
Yao, Nagarajan; Cold Forging Method for Polymer Microfabrication; Department of Mechanical Engineering, Oakland University, Rochester, MI 48309; Polymer Engineering and Science (Oct. 2004) vol. 44, No. 10, pp. 1998-2004, 7 pages.
Yao, Nagarajan, Li, Yi; A Two-Station Embossing Process for Rapid Fabrication of Surface Microstructures on Thermoplastic Polymers; School of Polymer, Textile & Fiber Eng., Georgia Institute of Technology, Atlanta, GA 30332 and Department of Industrial, Welding and Systems Engineering, The Ohio State University, Columbus, OH 43210; Polymer Engineering and Science (2007) vol. 47, No. 4, pp. 530-539, 10 pages; Wiley InterScience; Society of Plastics Engineers.
Yao, Kuduva-Raman-Thanumoorthy; An enlarged process window for hot embossing; School of Polymer, Textile & Fiber Eng., Georgia Institute of Technology, Atlanta, GA 30332; Journal of Micromechanics and Microengineering (2008) vol. 18, pp. 1-7; 7 pages; IOP Publishing Ltd.
All Office Actions and Reponses for U.S. Appl. No. 12/722,020, filed Mar. 11, 2010.

* cited by examiner

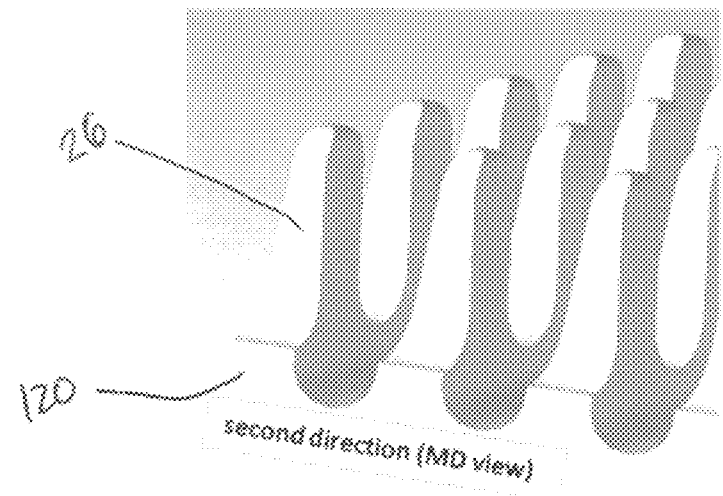
FIG. 21A
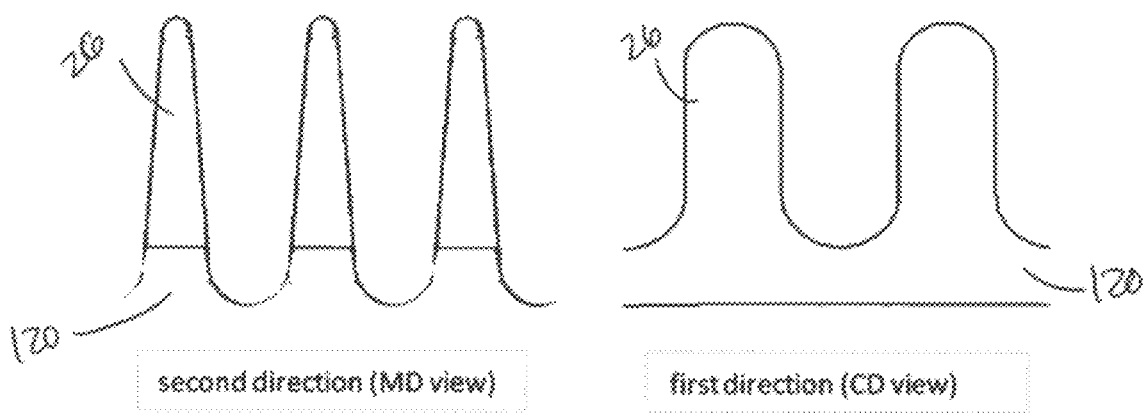
FIG. 21B  FIG. 21C

FORMED WEB COMPRISING CHADS

FIELD OF THE INVENTION

The present invention is directed to a formed web having chads. The chads may be formed in films or film-nonwoven laminates.

BACKGROUND OF THE INVENTION

Webs, such as thermoplastic films, have a variety of uses including component materials of absorbent articles (such as topsheets and backsheets), packaging (such as flow wrap, shrink wrap, and polybags), trash bags, food wrap, dental floss, wipes, electronic components, and the like. For many of these uses of webs, it can be beneficial for the web to have a textured, three-dimensional surface which can provide the surface of the web with a desirable feel (e.g., soft, silky), visual impression, and/or audible impression, as well as one or more desirable properties, such as improved fluid handling or strength. Webs exhibiting a desirable feel can be made via a vacuum forming process, a hydroforming process, an embossing process, or the like.

There is a need to develop webs having a desirable feel, visual impression, and/or audible impression as well as additional properties. In the case of webs used in absorbent articles, it is desirable for a single portion of the web to comprise dual, or more, properties (such as improved softness, fluid handling, or other properties) in a predetermined location on the web.

SUMMARY OF THE INVENTION

A formed web comprising discrete three-dimensional elements formed therein, wherein at least some of the discrete three-dimensional elements comprise chads with corresponding apertures, wherein the aperture has a perimeter, wherein the chad has a length, wherein the chads are attached along a portion of the aperture perimeter which forms a connection segment, wherein the connection segment is less than about 50% of the entire aperture perimeter, and wherein the web comprises a film.

BRIEF DESCRIPTION OF THE DRAWINGS

The following detailed description of specific embodiments of the present invention can be best understood when read in conjunction with the drawings enclosed herewith.

FIGS. 21A-C illustrate the teeth of Examples 1, 2, and 3;

DETAILED DESCRIPTION

Figure 1A:
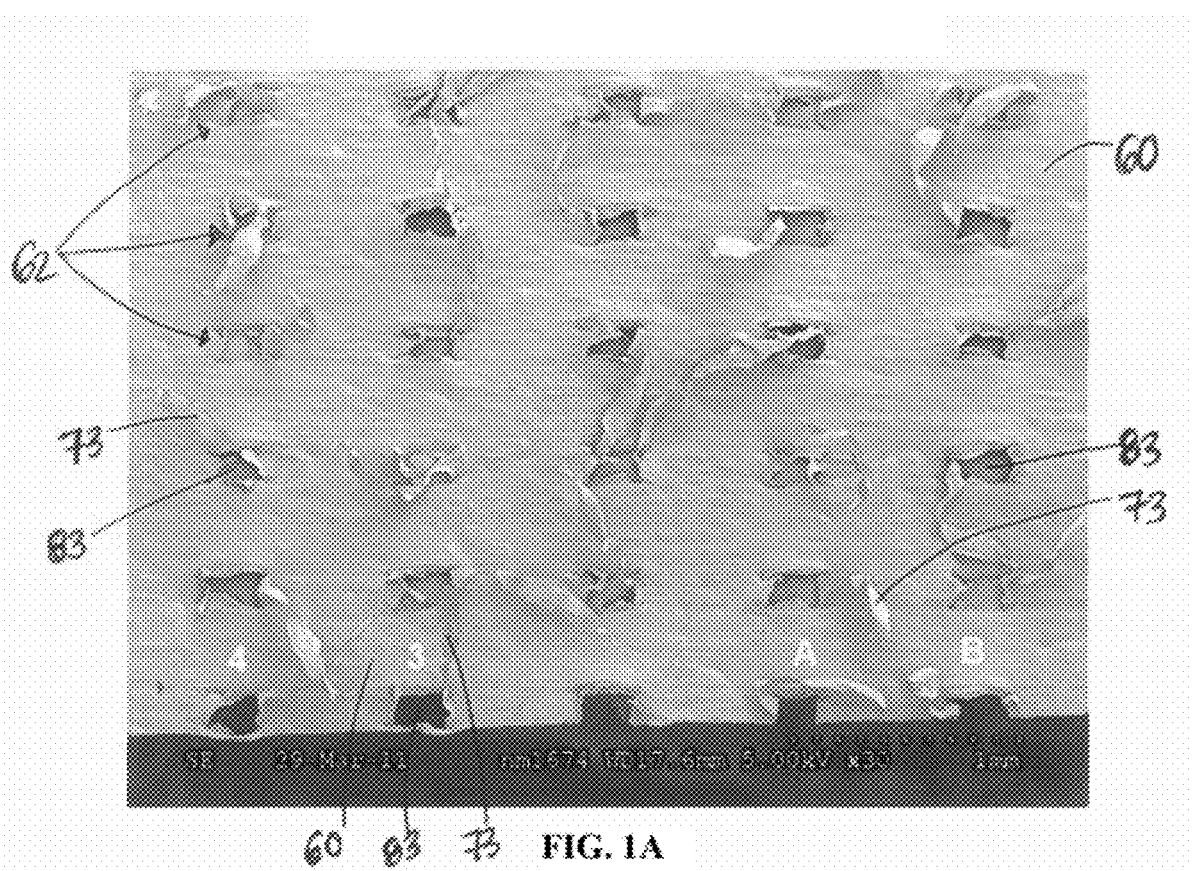
FIGS. 1A and 1B are images of a web which comprises chads.

The present invention is directed to a web that overcomes one or more of the aforementioned shortcomings of the prior art. Compared to prior art webs, embodiments of the new web allow for the formation of a web which comprises discrete three-dimensional elements ("3-D elements") in the form of "chads," or flaps of web material, and associated apertures. The chads are only partially attached to the perimeter of the corresponding aperture and therefore provide desirable softness due to the chads' ability to bend and hinge. In the case of webs used in absorbent articles, such new structures may include those that provide a single portion of the web with multiple properties (such as improved softness, fluid handling, or other properties) in a predetermined location on the web.

Precursor Web

A precursor web 50 is converted into a formed web 60 according to the process described below. Suitable precursor webs 50 include materials that can be deformed beyond their yield point by the strain put on the web in the deformation zone of the process, such that the precursor web 50 is forced to conform between the forming elements 10 of the forming structures 110, 120 to produce a web 60 having discrete three-dimensional elements ("3-D elements") 62. Precursor web 50 comprises a film, such as polymeric or thermoplastic film, and is optionally laminated with cellulose, foils, such as metallic foils (e.g. aluminum, brass, copper, and the like), polymeric or thermoplastic films, webs comprising sustainable polymers, foams, fibrous nonwoven webs comprising synthetic fibers (e.g. TYVEK®), collagen films, chitosan films, rayon, cellophane, and the like. Suitable films include both cast and blown. Webs 50 can be similar to those described in U.S. application Ser. No. 12/879,567. The thickness of the precursor web 50 prior to forming will typically range from 5 to 150 microns, 10 to 100 microns, or 15 to 50 microns. Other suitable thicknesses include 10, 15, 20, 25, or 30 microns.

Thermoplastic precursor webs 50 will typically have a yield point and the precursor web 50 is preferably stretched beyond its yield point to form a web 60. That is, the precursor web 50 should have sufficient yield properties such that the precursor web 50 can be strained without rupture to an extent to produce the desired discrete 3-D elements 62. As disclosed below, process conditions such as temperature can be varied for a given polymer to permit it to stretch with or without rupture to form the web 60 having the desired discrete 3-D elements 62. In general, therefore, it has been found that preferred starting materials to be used as the precursor web 50 for producing the web 60 exhibit low yield and high-elongation characteristics. Examples of films suitable for use as the precursor web 50 comprise low density polyethylene (LDPE), linear low-density polyethylene (LLDPE), and blends of linear low-density polyethylene and low density polyethylene (LLDPE/LDPE).

At least a portion of two precursor webs 50 may be joined by an embossed seal, the seal including co-registered concentric discrete 3-D elements formed in the at least two webs, the discrete 3-D elements having open proximal ends. See US 2010/0233428 and U.S. application Ser. No. 12/879,531 for more details on sealing film/film, film/nonwoven, and quiet seals.

The precursor web 50 can also optionally include colorants, such as pigment, lake, toner, dye, ink or other agent used to impart a color to a material, to improve the visual appearance of the web 60. Suitable pigments herein include inorganic pigments, pearlescent pigments, interference pigments, and the like. Non-limiting examples of suitable pigments include talc, mica, magnesium carbonate, calcium carbonate, magnesium silicate, aluminum magnesium silicate, silica, titanium dioxide, zinc oxide, red iron oxide, yellow iron oxide, black iron oxide, carbon black, ultramarine, polyethylene powder, methacrylate powder, polystyrene powder, silk powder, crystalline cellulose, starch, titanated mica, iron oxide titanated mica, bismuth oxychloride, and the like. Suitable colored webs are described in US 2010/0233438 and US 2010/0233439. Precursor webs 50 can include various optional ingredients, such as those described in U.S. application Ser. No. 12/879,567.

Formed Web

Figure 1B:
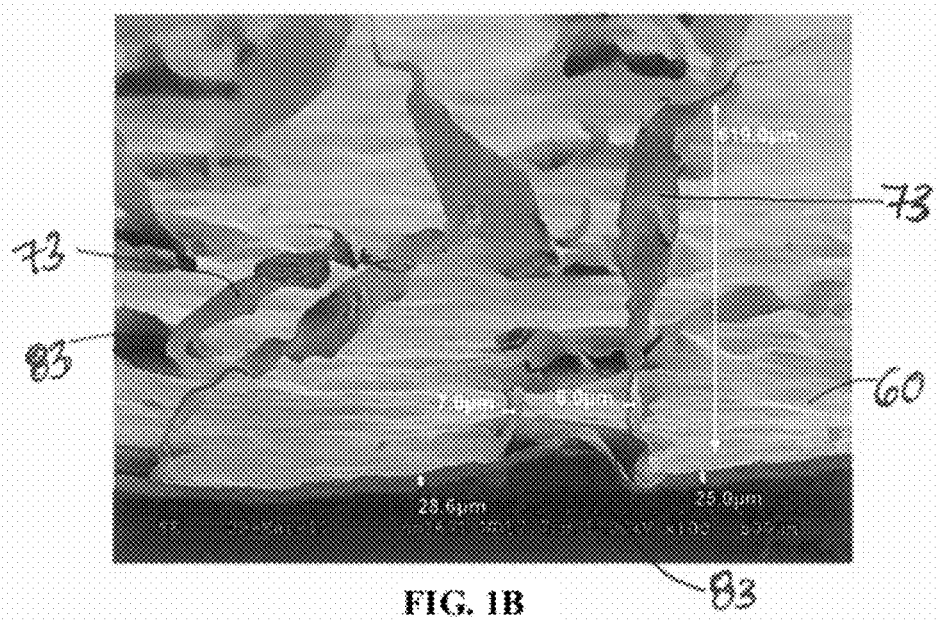
Figure 2A:
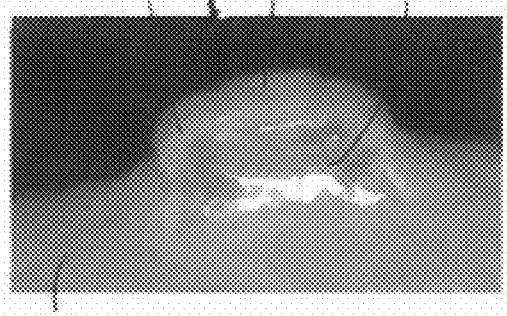
FIGS. 2A-E are examples of discrete three-dimensional elements.
Figure 2B:
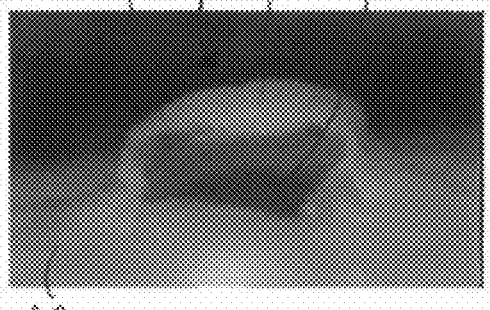
Figure 2C:
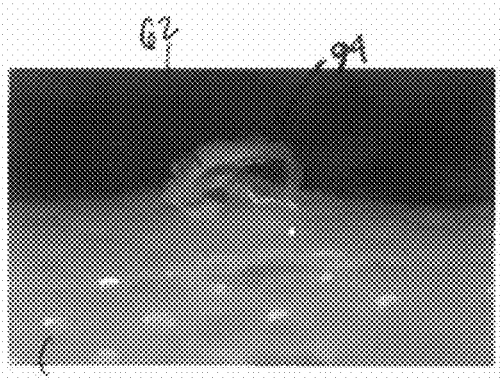
Figure 2D:
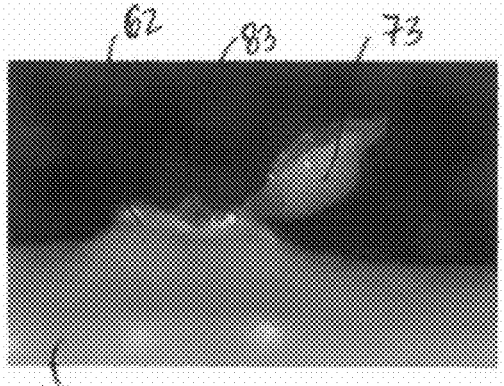
Figure 2E:
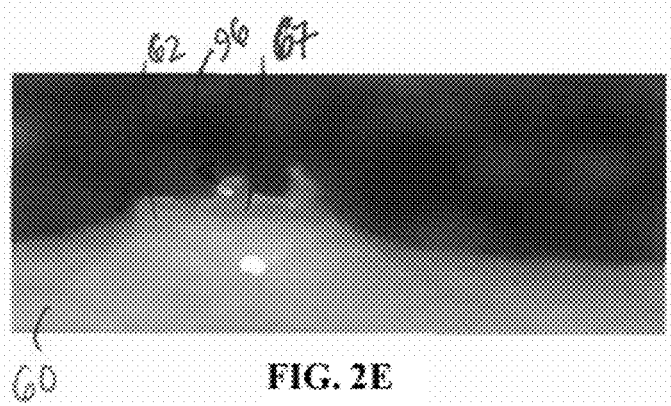
Figure 3:
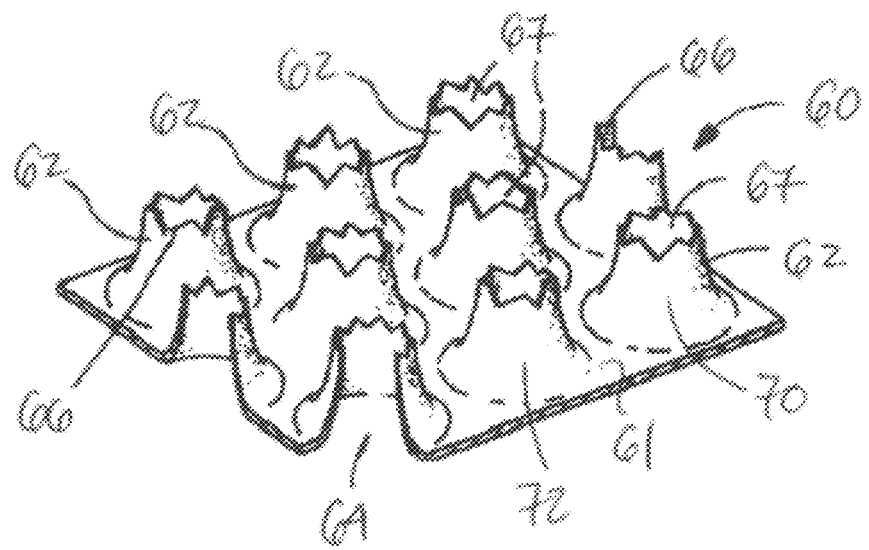
FIG. 3 is a perspective view of a portion of a web.
Figure 4:
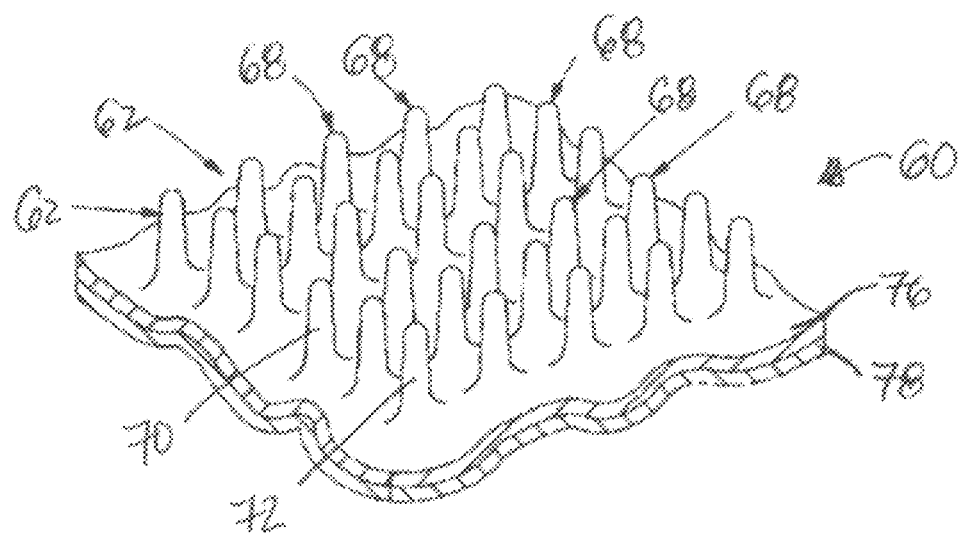
FIG. 4 is a perspective view of a portion of another web.

A precursor web 50 is processed according to the process of the disclosure to form a formed web 60 that can have various desired structural features and properties such as desired soft hand feel, an aesthetically pleasing visual appearance, and improved sound effects (e.g., when handled or manually manipulated, the web 60 may create less sound as compared to the precursor web 50). A pair of mated forming structures 101 is provided to conform the precursor web 50 between the forming elements 10 of the first and second forming structures 110,120. A first web 60 having discrete three-dimensional elements ("3-D elements") 62 is thereby produced, as shown in FIG. 1A. FIG. 1B shows an enlarged view of the 3-D element 62 shown at "3" in FIG. 1A; specifically, the 3-D element 62 is a chad 73. Other exemplary discrete 3-D elements 62 are pictured in FIGS. 2A-E. FIG. 2A shows a bubble 90 wherein the sidewalls are thinned in the cross direction. FIG. 2B shows a hood 92, FIG. 2C a ribbon 94, FIG. 2D a chad 73, and FIG. 2E a crater 96. The discrete 3-D elements 62 are formed as protruded extensions of the web 60, generally on a first surface 76, a second surface 78, or both surfaces thereof. As such, the discrete 3-D elements 62 can be described as being integral with web 60, and formed by permanent local plastic deformation of the precursor web 50. The discrete 3-D elements 62 can be described as having sidewalls 70 defining an open proximal end 64 and open 67 (e.g., FIG. 3) or closed 68 (e.g., FIG. 4) distal ends.

The discrete 3-D elements 62 each have a height h measured from a minimum amplitude $A_{min}$ between adjacent 3-D elements 62 to a maximum amplitude $A_{max}$ at the closed or open distal end 66. The discrete 3-D elements 62 have a diameter d, which for a generally cylindrical structure is the outside diameter at a lateral cross-section. By "lateral" is meant generally parallel to the plane of the first surface 76. For generally columnar discrete 3-D elements 62 having non-uniform lateral cross-sections, and/or non-cylindrical structures of discrete 3-D elements 62, diameter d is measured as the average lateral cross-sectional dimension at ½ the height h of the discrete 3-D element. Thus, for each discrete 3-D element, an aspect ratio, defined as h/d, can be determined. The discrete 3-D element can have an aspect ratio h/d of at least 0.2, at least 0.3, at least 0.5, at least 0.75, at least 1, at least 1.5, at least 2, at least 2.5, or at least 3. The discrete 3-D elements 62 will typically have a height h of at least 30 microns, at least 50 microns, at least 65 microns, at least 80 microns, at least 100 microns, at least 120 microns, at least 150 microns, or at least 200 microns. Or, the discrete 3-D elements 62 can have taller heights h of up to 5 cm, 2.5 cm, up to 2 cm, up to 1.5 cm, up to 1 cm, up to 0.5 cm, up to 0.1 cm, or up to 0.02 cm. The 3-D elements 62 will typically be at least the same height as the thickness of the precursor web 50, or at least two times the thickness of the precursor web 50, or preferably at least three times the thickness of the precursor web 50. The discrete 3-D elements 62 may have a diameter d of 50 microns to 790 microns, 50 microns to 600 microns, 50 microns to 500 microns, 65 microns to 400 microns, or 75 microns to 300 microns. Or, the discrete 3-D elements 62 can have larger diameters up to 2.5 cm, up to 2 cm, up to 1.5 cm, up to 1 cm, up to 0.5 cm, up to 0.1 cm, or up to 0.08 cm. For discrete 3-D elements 62 that have generally non-columnar or irregular shapes, a diameter of the discrete 3-D elements can be defined as two times the radius of gyration of the discrete 3-D elements at ½ height. In one embodiment, the diameter of a discrete 3-D element is constant or decreases with increasing amplitude (amplitude increases to a maximum at closed or open distal end 66). The diameter, or average lateral cross-sectional dimension, of the discrete 3-D elements 62 can be a maximum at proximal portion and the lateral cross-sectional dimension steadily decreases to distal end. This structure 110,120 is desirable to help ensure the web 60 can be readily removed from the forming structures 110,120.

Thinning of the precursor web 50 can occur due to the relatively deep drawing required to form high aspect ratio discrete 3-D elements 62. For example, thinning can be observed at the closed 68 or open 67 distal ends 66 and/or along the sidewalls 70. By "observed" is meant that the thinning is distinct when viewed in magnified cross-section. Such thinning can be beneficial as the thinned portions offer little resistance to compression or shear when touched. For example, when a person touches the web 60 on the side exhibiting discrete 3-D elements 62, the fingertips of the person first contact the closed or open distal ends 67 of the discrete 3-D elements 62. Due to the high aspect ratio of the discrete 3-D elements 62, and the wall thinning of the precursor web 50 at the distal ends 66 and/or along the sidewalls 70, the discrete 3-D elements 62 offer little resistance to the compression or shear imposed on the web 60 by the person's fingers.

Thinning of the formed web 60 at the distal ends 66 and/or along the sidewalls 70 can be measured relative to the thickness of the precursor web 50 or relative to the thickness of the land area 61 that completely surrounds the discrete 3-D elements 62 of the web 60. The web 60 or 3-D elements 62 will typically comprise at least a portion which exhibits thinning of at least 25%, at least 50%, or at least 75% relative to the thickness of the precursor web 50. The web 60 or 3-D elements 62 will typically comprise at least a portion which exhibits thinning of at least 25%, at least 50%, at least 75%, or at least 85% relative to the thickness of the land area surrounding the discrete 3-D elements 62 of the web 60. In some cases, there is relatively little thinning at the distal end 66, e.g., when using protrusions 20 which are not relatively sharp. In such instances, it is believed that friction lock occurs, leading to relatively more thinning on the sidewalls 70.

Figure 5:
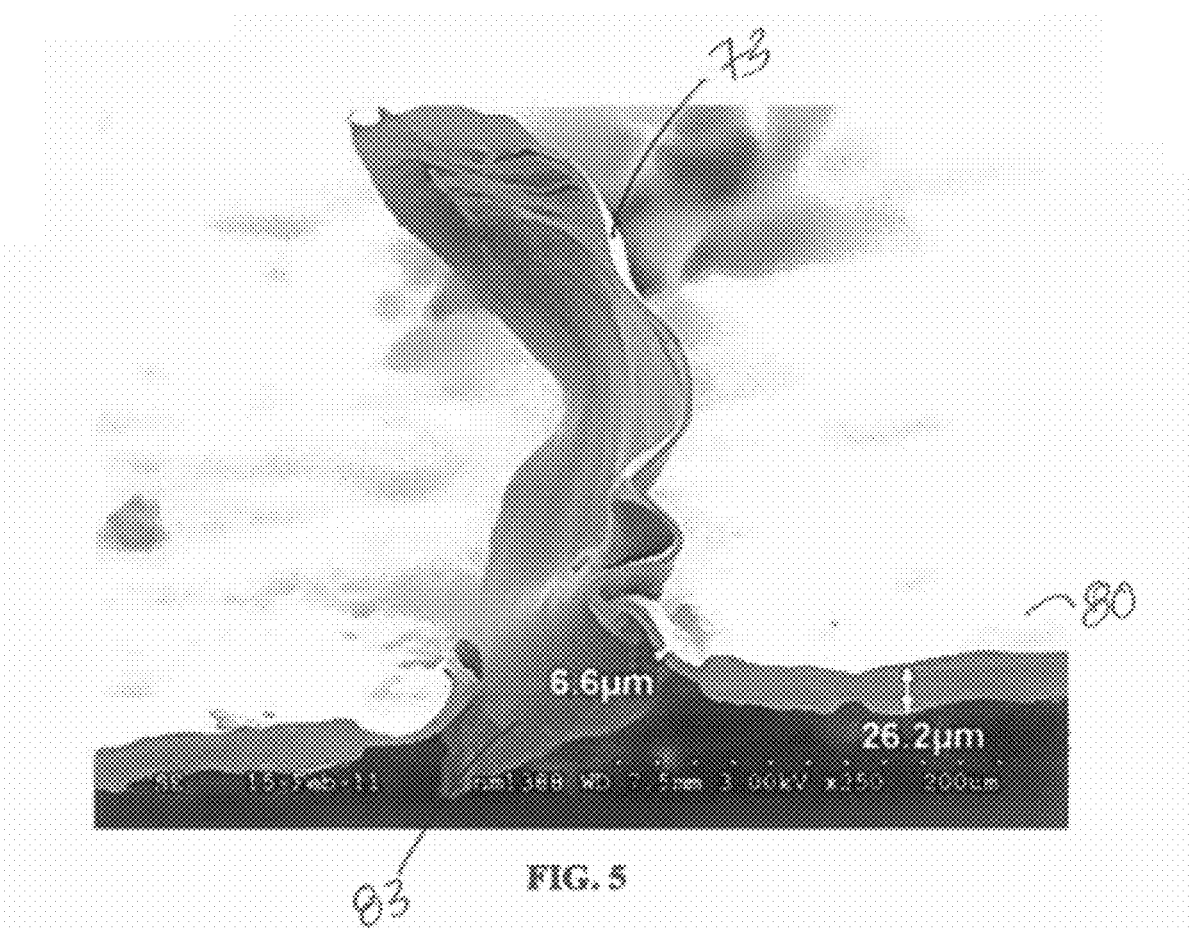
FIG. 5 is an image of a web comprising a chad.

A desirable feeling of softness, such as like the feeling of a velour fabric, is achieved when at least some of the discrete 3-D elements 62 comprise chads 73, shown in FIGS. 1A, 1B, 2D, and 5. Chads 73 are formed when at least a portion of a sidewall 70 thins and ruptures, leaving an aperture 83 and a flap of web material, or chad 73, attached to a web 60, as shown in FIG. 5. If a film laminate with a fibrous structure is used, precursor web 50 should be orientated such that web 60 will not comprise fibers protruding above the plane of the aperture 83 of the chad 73. No fibers protrude into or through the aperture 83 in the direction of the chad 73.

Unlike the other 3-D elements 62 described herein, chads 73 are only partially connected to the perimeter of the apertures $P_a$. In one embodiment, $P_a$ is equal to about the aperture diameter d multiplied by $\pi$. The chads 73 are attached at a connection segment CS along a portion of the aperture perimeter $P_a$. This enables the chads 73 to move more freely in more directions than 3-D elements 62 that are attached around the entire perimeter or at two or more connection segments along an aperture perimeter. The connection segment CS may be located on any portion of the perimeter of the aperture $P_a$ relative to the machine direction. The connection segment CS is less than about 50%, less than about 40%, less than about 30%, less than about 20%, or less than about 10% of the entire aperture perimeter $P_a$. As the length of the connection segment CS gets shorter and shorter, the chad 73 can more easily hinge, move, bend, or rotate about its connection segment CS. Preferably, chads 73 are hingeable about the connection segment CS.

Figure 6:
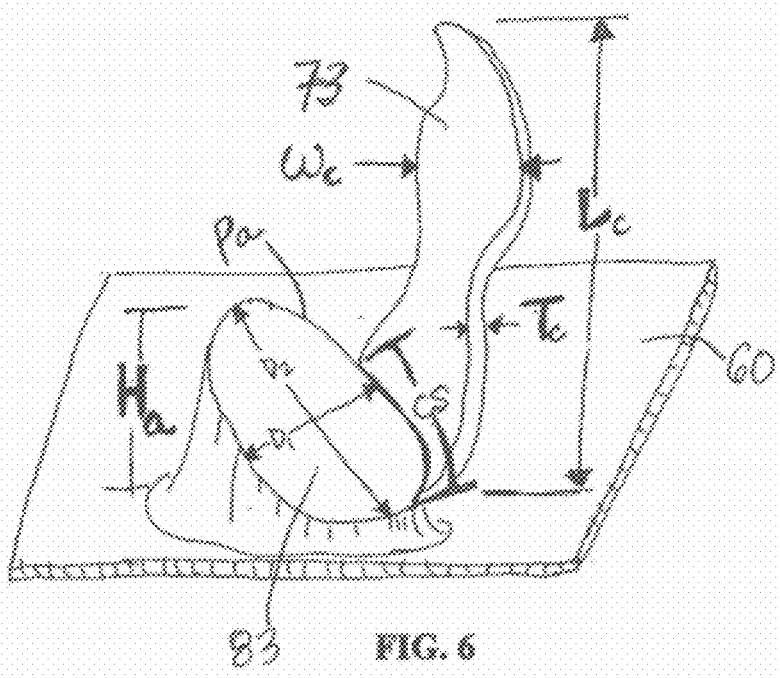
FIG. 6 is an illustration of a chad.

A 3-D element may comprise one chad 73 per aperture 83 or more than one chad 73 per aperture 83. In a preferred embodiment, there is one chad 73 per aperture 83. The aperture 83 may be flush with the web surface 76, or it may be above the plane of the web surface 76, such as in the form of a crater (e.g., FIG. 2D). Thus, the aperture 83 may have a height $H_a$. As shown in FIG. 6, the chads 73 will typically have a length $L_c$ (when extended from its connection segment) of at least 30 microns, or at least 65 microns, or at least 100 microns, at least 200 microns, at least 300 microns, at least 400 microns, at least 500 microns, at least 600 microns, or at least 700 microns. Or, the chads 73 can have larger lengths $L_c$ of up to 7.5 cm, 5 cm, 2.5 cm, 2 cm, 1.5 cm, 1 cm, 0.5 cm, 0.1 cm, or up to 0.08 cm. Or, the chads 73 may have a length $L_c$ of at least two times, three times, four times, or up to ten times the diameter d of the aperture 83. The thickness $T_c$ of a chad 73 may vary along the length $L_c$ of the chad 73. The width of the chad 73 can be wider, narrower, or similar to the connection segment CS length. The width $W_c$ of the chad 73 may be measured at ½ the length $L_c$ of the chad 73. The chads 73 have an aspect ratio $AR_c=L_c/W_c$. $AR_c$ can be greater than 0.5, 0.75, 1, 1.5, 2, 3, or 4. As the aspect ratios $AR_c$ of the chads 73 of the web increase, the web will become softer. The center-to-center spacing of a chad 73 and another 3-D element 62 (which may or may not be another chad 73) is measured from the center of the chad's aperture 83. Preferably, chads 73 are bendable at various points along their length $L_c$.

The number, size, and distribution of chads 73 on the web 60 can be predetermined based on desired soft feel and visual effects. At least some, at least 25%, at least 50%, at least 75%, at least 95%, or all of the 3-D elements 62 formed in the web are chads 73. For applications such as a topsheet, backsheet, or release paper wrapper in disposable absorbent articles, or packaging, it can be desired that the chads 73 protrude only from one surface of web 60. Therefore, when the web 60 is used as a topsheet in a disposable absorbent article, the web 60 can be oriented such that the chads 73 are skin contacting for superior softness impression. In other embodiments, it will be desired to have chads 73 on both the first surface 76 and second surface 78 of the web 60. In the case of webs used in absorbent articles, such new structures may include those that provide a single portion of the web with multiple properties (such as improved softness, fluid handling, or other properties) in a predetermined location on the web. Chads 73 do not typically have areas the same as their apertures 83 and thus would not make good one-way valves.

The chads 73 will typically comprise at least a portion which exhibits thinning of at least 25%, at least 50%, or at least 75% relative to the thickness of the precursor web 50. The chads 73 will typically comprise at least a portion which exhibits thinning of at least 25%, at least 50%, at least 75%, or at least 85% relative to the thickness of the land area surrounding the chads 73. In a preferred embodiment, the chads 73 comprise at least a portion which exhibits thinning of at least 75% relative to the thickness of the land area surrounding the chads 73. To achieve desirable web softness, thinning can be maximized to obtain long and narrow chads 73. The change in caliper of the web 60 resulting from chads 73 is very little (however, crater-type apertures 83 may change the caliper of the web 60). One reason chads 73 may not change the bulk caliper of the web much, if at all, is because the chads 73 may lie down on top of the web 60 (e.g., touching the web or parallel to it) rather than rising perpendicular to the web 60. This may be due to the thin and flimsy nature of the chads 73 and/or the web 60 undergoing further processing (e.g., folding, packaging). At least a portion of a chad 73 (in addition to the connection segment portion) may touch the web 60; e.g., an absorbent article may comprise a topsheet which comprises chads which lie flat against the topsheet's body-contacting surface.

The "area density" of the discrete 3-D elements 62, which is the number of discrete 3-D elements 62 per unit area of first surface 76, can be optimized and the web 60 may include about 200 to about 3,000; or about 200 to about 10,000; about 220 to 8,000; about 240 to about 6,000; about 300 to about 5,000; or about 350 to about 3,000 discrete 3-D elements 62 per square centimeter. Or, the web 60 may include about 0.1 to about 10,000, 4 to about 10,000, about 95 to about 10,000, about 240 to about 10,000, about 350 to about 10,000, about 500 to about 5,000, or about 700 to about 3,000 discrete 3-D elements 62 per square centimeter. In general, the center-to-center spacing can be optimized for adequate tactile impression, while at the same time minimizing entrapment of materials, such as fluids, between discrete 3-D elements 62 when the web is used, e.g., as a topsheet. The center-to-center spacing C between adjacent discrete 3-D elements 62 can be less than about 800 microns or greater than about 800 microns. Other acceptable center-to-center spacings are from about 30 microns to about 700 microns, about 50 microns to about 600 microns, about 100 microns to about 500 microns, or about 150 microns to about 400 microns. Further acceptable center-to-center spacings are about 30 microns to about 32,000 microns, about 100 microns to about 5,000 microns, about 150 microns to about 1,000 microns, about 150 microns to about 600 microns, or about 180 microns to about 500 microns.

Figure 7:
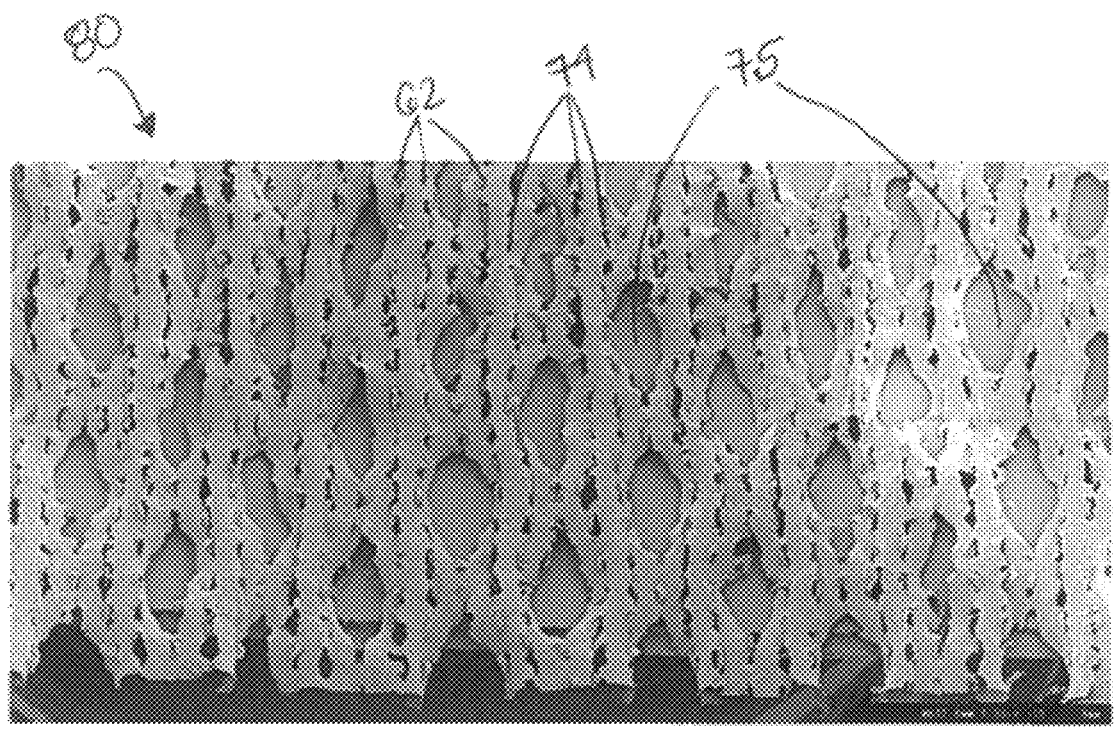
FIG. 7 shows another web which comprises chads.

A second web 80 having second discrete 3-D elements 74 and/or third discrete 3-D elements 75 in addition to the first discrete 3-D elements 62 may be produced, as described below and shown in FIG. 7. The various 3-D elements 62,74,75 may be the same, similar, different, or combinations thereof. The second discrete 3-D elements 74 and/or third discrete 3-D elements 75 can be formed adjacent to, in between, or at least partially overlapping with, the first discrete 3-D elements 62. They may be formed on various sides of a web. Location of the 3-D elements may vary—e.g., the middle, perimeter, in zones, etc, of the web. The first discrete 3-D elements 62, second discrete 3-D elements 74, and/or third 3-D elements 75 can be various sizes and have various combinations of open and closed distal ends. In one embodiment the first discrete 3-D elements 62 and second discrete 3-D elements 74 have closed distal ends 68, while the third discrete 3-D elements 75 have open distal ends. In one embodiment, a formed web 80 comprises first discrete 3-D elements in the form of chads 73, second 3-D elements in the form of macro-cones 74, third 3-D elements in the form of tufts 75, as well as regions with no 3-D elements. The chads 73 may be formed on the first, or body-facing, surface 76 of a web 60; macro-cones 74 may be formed on the second, or non-body facing, surface 78 of the web 80; and tufts 75 may be formed on the first surface 76 of the web 80. Chads 73 may be a micro-texture located on the entire web 60, while macro-cones 74 may be a macro-texture located in a center region of the web, and tufts 75 may be a macro-texture located in a perimeter region. US 2010/0036338 A1 provides other webs which may be combined with chads 73.

Forming Structures

Figure 8:
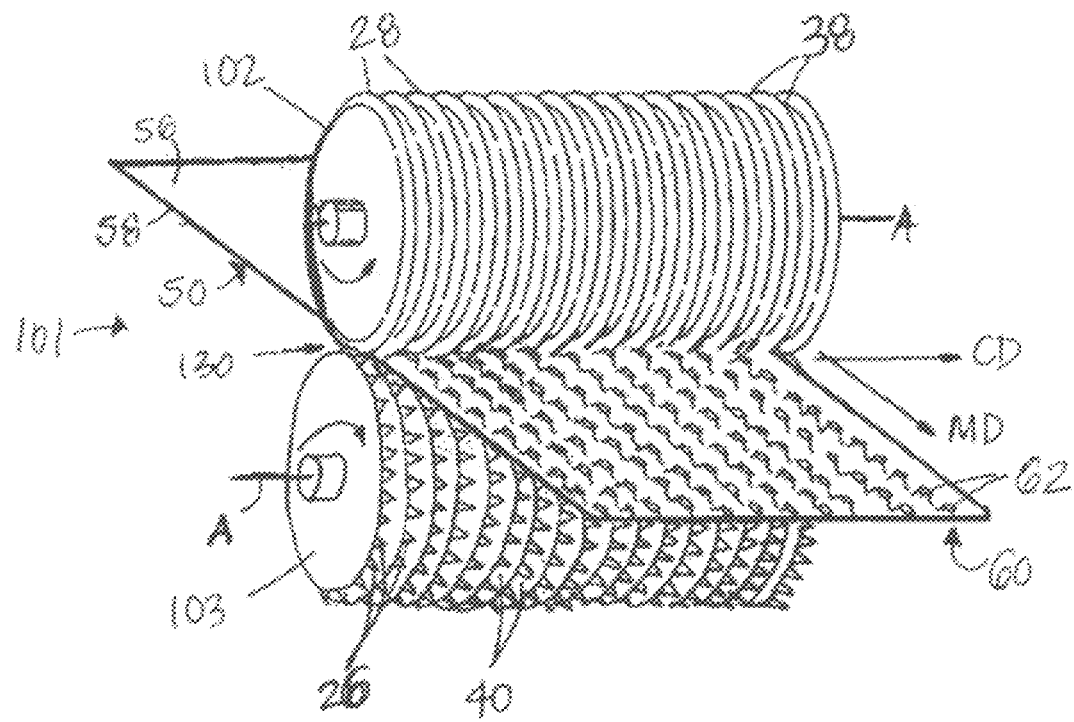
FIG. 8 is a perspective view of a pair of mated forming structures.
Figure 9:
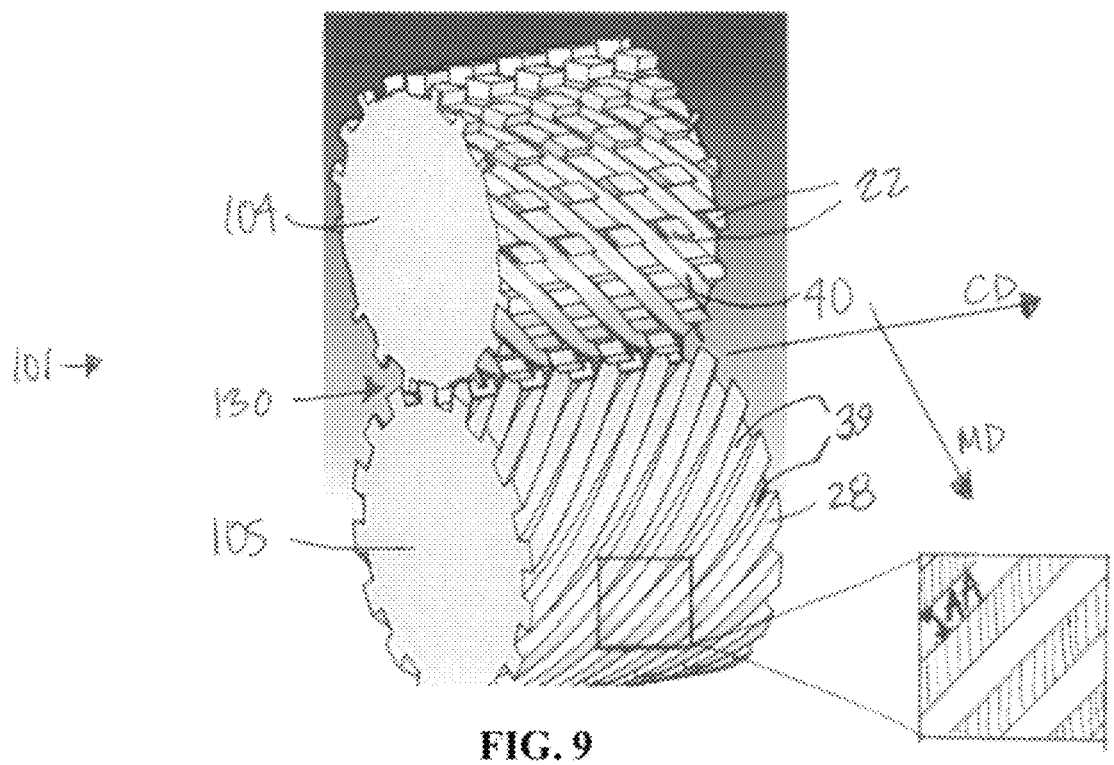
FIG. 9 is a perspective view of another pair of mated forming structures.
Figure 10:
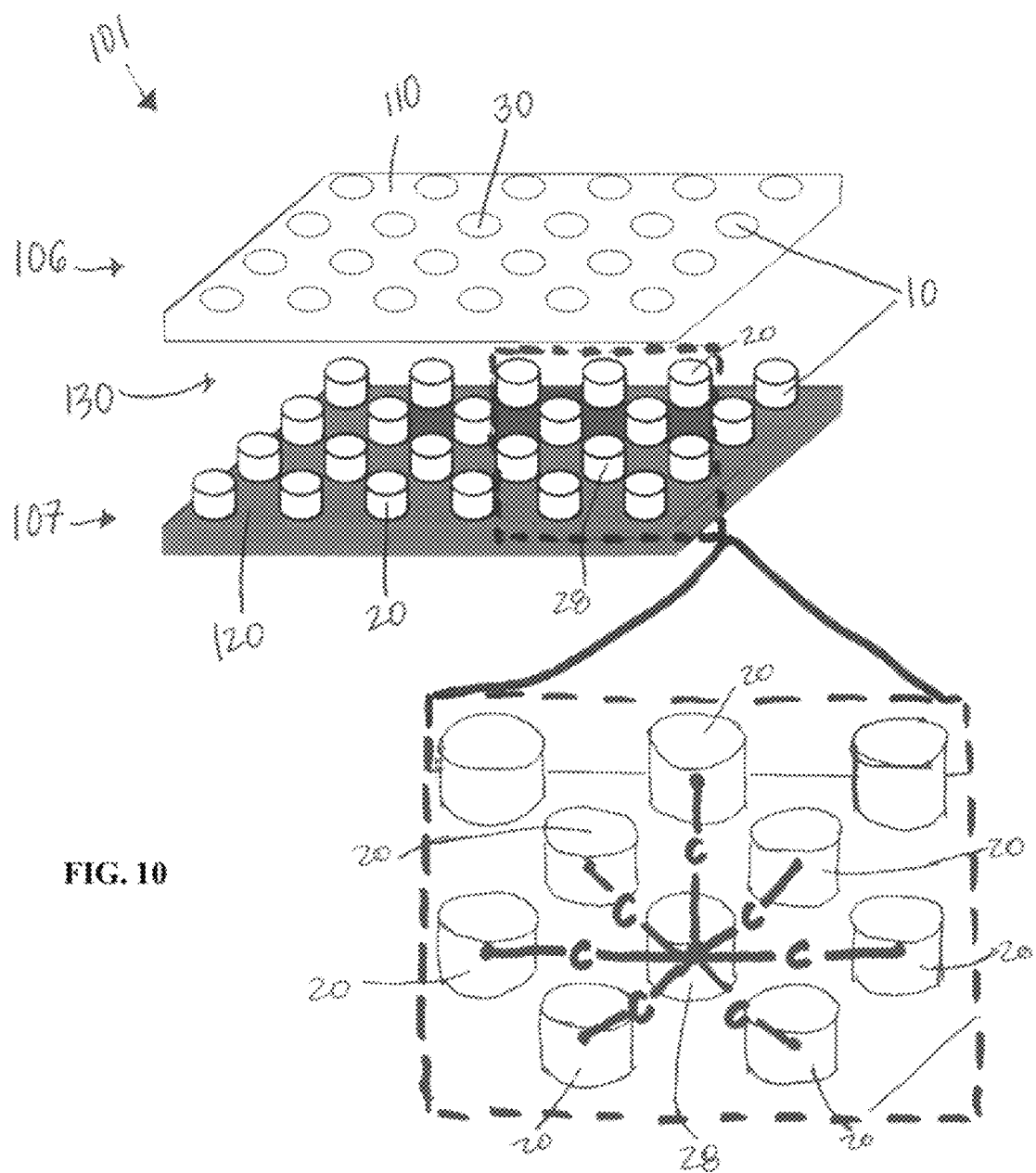
FIG. 10 is a perspective view of another pair of mated forming structures.
Figure 11A:
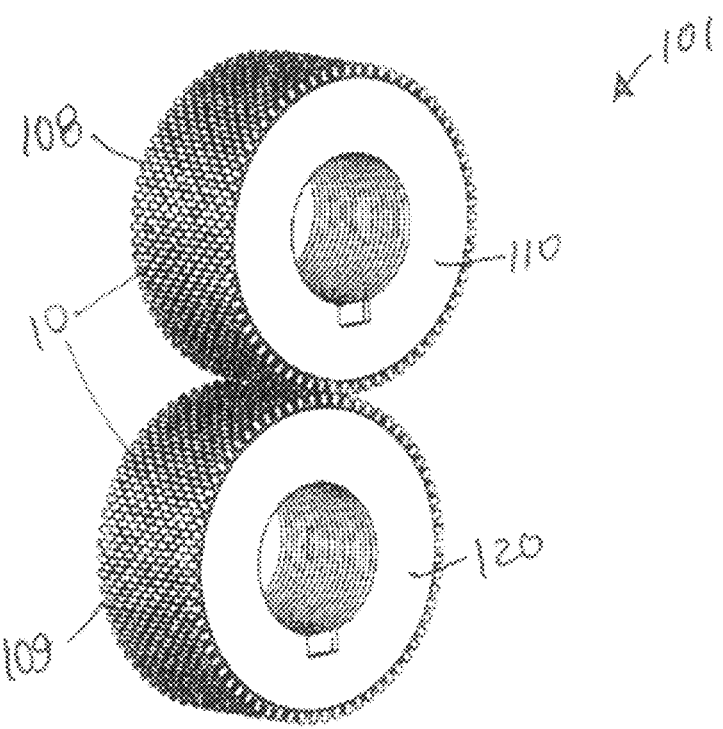
FIGS. 11A and 11B are perspective views of another pair of mated forming structures.
Figure 11B:
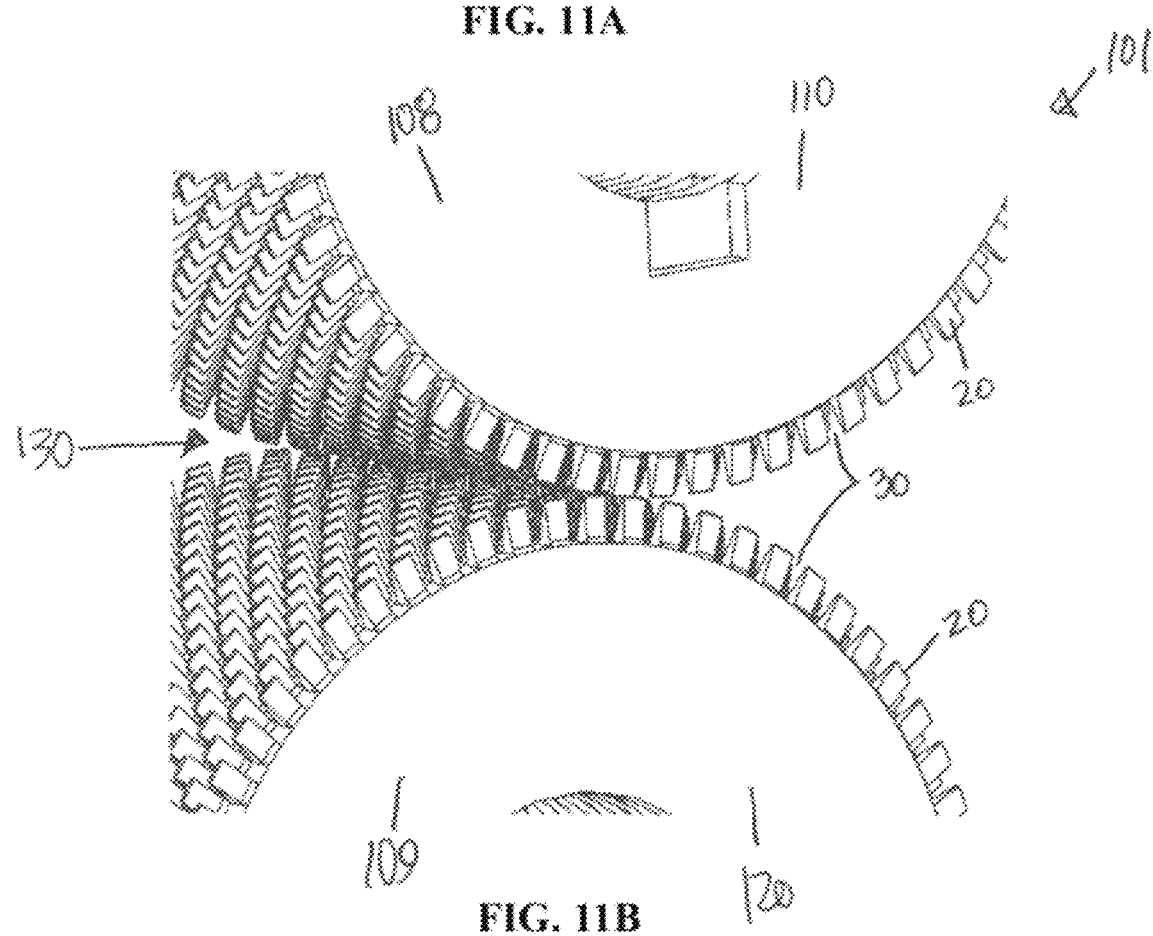

The forming process can be carried out via an apparatus that comprises a pair of rigid mated forming structures, such as those shown in FIGS. 8-10. Forming structures may comprise rollers, plates, belts, sleeves, or the like, or combinations thereof. Suitable pairs of forming structures 101 include, but are not limited to: a pair of counter-rotating rollers that define a nip therebetween, a pair of plates, and a pair of belts. In one embodiment, as shown in FIG. 8, the pair of mated forming structures 101 is a pair of counter-rotating rollers 102,103 which engage in the machine direction MD. Using a forming apparatus with rollers can be beneficial in the case of continuous processes, particularly those in which the speed of the process is of interest. In another embodiment, as shown in FIG. 9, the pair of mated forming structures 101 is a pair of counter-rotating rollers 104,105 which engage at an angle AA from the machine direction MD. In another embodiment, as shown in FIG. 10, the pair of mated forming structures 101 is a pair of plates 106,107. In another preferred embodiment, the pair of mated forming structures may comprise an endless belt. Referring to FIGS. 10, 11A, and 11B, individual forming structures 110,120 (or any additional forming structures 210,220 of additional texturing steps) for use in the process of the present disclosure include a plurality of forming elements 10. As used herein, "forming structures" refer generally to structures capable of imparting a texture to a web. As used herein, "forming elements" refer generally to elements that provide texture to a web; types of forming elements include discrete protrusions, discrete voids, continuous voids, or combinations thereof. Forming elements may vary in shape, size, sharpness, taper, aspect ratio, and/or center-to-center spacing. One type or multiple types of forming elements 10 can be present on a single forming structure. Generally, a pair of mated forming structures comprises at least two types of forming elements. For example, the first forming structure 110 may include voids 30 while the second forming structure 120 may include protrusions 20. Alternatively, the first and second forming structures 110,120 may have the same type of forming elements 10; for example, both forming structures 110,120 can include protrusions 20 and voids 30, as illustrated in FIGS. 11A and 11B. In the embodiment shown in FIG. 11B, the spaces between adjacent protrusions 20 act as voids 30. The term "adjacent," as used herein, with reference to features or regions, means near or close to, and which need not be in contact with each other.

Figure 12:
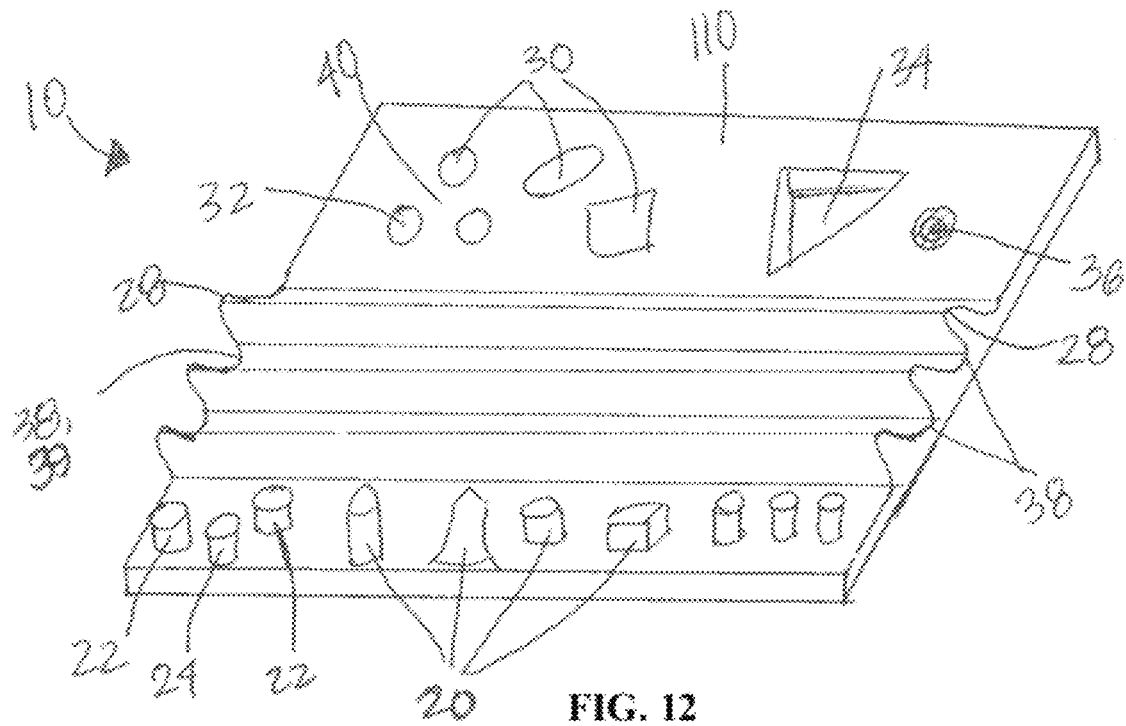
FIG. 12 is a perspective view of a portion of a forming structure.

As illustrated in FIG. 12 the forming elements 10 of either or both of the first and second forming structures 110,120 can include protrusions 20 or voids 30 selected from discrete protrusions 22 (e.g., pillars 24 or teeth 26), ridges 28, discrete voids 32 (e.g., apertures 34 or depressions 36), continuous voids 38, grooves 39, or a combination thereof. The forming structures 110,120 can further include lands 40 completely surrounding the forming elements 10. The forming elements 10 of the forming structures 110,120 can be small in scale relative to typical patterns used on forming structures 110,120 in conventional texturing or embossing processes. The process of the disclosure can produce webs 60 that include relatively high aspect ratio 3-D elements 62 with thinned distal ends 66 and/or sidewalls 70, even without heating webs and even at high speeds.

Figure 13:
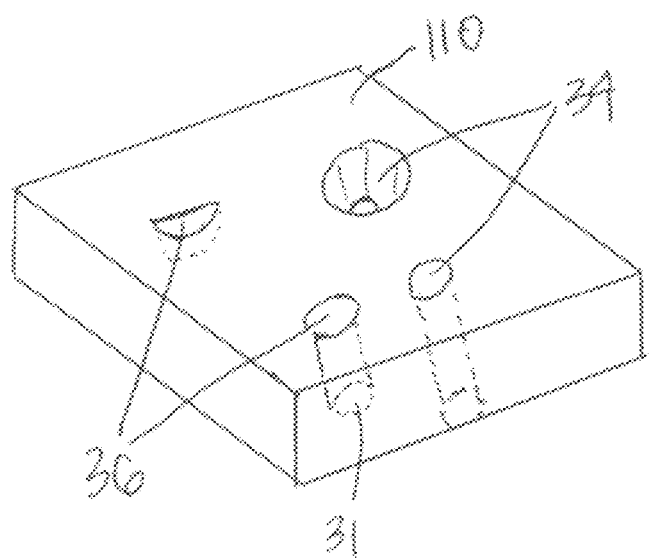
FIG. 13 is a perspective view illustrating apertures and depressions.

FIG. 13 illustrates the distinction between two exemplary types of discrete voids 32 described herein: apertures 34 and depressions 36. As used herein, "apertures 34" refers to an opening in the forming structures 110,120 that does not include a bottom surface limiting the depth of the opening. In contrast, as used herein, "depressions 36" refers to an opening in the forming structures 110,120 having a bottom surface, or valley 31, limiting the depth of the opening to be less than the thickness of the forming structures 110,120. The valley 31 can be, for example, porous or non-porous. The valley 31 can include an opening having a width smaller than the diameter of the depression 36, which vents the depression 36 by allowing air to pass through the depression 36. For example, the valley 31 opening may have a width smaller than the thickness of the precursor web 50. The valley 31 can be flat, rounded, or sharp.

As used herein, "grooves 39" are voids 30 which are non-circular in cross-section, have a length greater than a width, and are sized to encompass one or more protrusions 20. The length of the grooves 39 may be aligned with a machine direction MD or cross direction CD, or skewed a certain degree from the machine direction or cross direction or combinations thereof. Referring back to FIG. 9, the pair of skewed rollers 104 comprises grooves 39. In certain embodiments, the grooves are skewed, meaning they run at an angle AA of 5° to 85°, 15° to 75°, 25° to 65°, or 45° from the machine direction. Engaging forming rollers at an angle skewed to the machine direction MD can result in structures which have greater strength and/or softness (as well as a different visual appearance than if it were machine direction-aligned only) depending upon the use of the web 60.

The forming structures 110,120 can be a solid roll, or have a thickness of 25 to 25,000 microns, or 100 to 5,000 microns. The voids 30 can have a depth of 10 to 500 microns, or 25 to 5000 microns, or even greater. The depth of the voids 30 should be at least as tall as the tallest protrusions 20. Preferably, the voids 30 have a depth that is at least three times the total thickness of the webs. The depth of an aperture 34 corresponds to the thickness of the forming structures 110,120 because the aperture 34 has no bottom surface limiting its depth.

The perimeter of the voids 30 on the web contacting surface of the forming structures 110,120 can have a straight edge or can have a radius of curvature as measured from the web contacting surface of the forming structures 110,120 into the void 30. The radius of curvature can be 0 to 2000 microns, preferably 0 to 25 microns, and more preferably 2 to 25 microns. In one embodiment, an angled taper, commonly known as a chamfer, is used. In one embodiment a combination of straight edges and radii are used.

The voids 30 have at least one diameter, which for a generally cylindrical structure is the inside diameter. For example, a discrete void 32 may take the shape of an oval, while a continuous void 38 may take the shape of a groove 39; each void having two diameters, one in the length direction and one in the width direction. The diameter of the void 30 may be sized to encompass one or more protrusions. FIGS. 14A-D illustrate exemplary combinations of voids 30 and protrusions 20. At an engagement position 140 of the forming structures 110,120, there is a sidewall clearance 42 and a tip-to-valley clearance 44 between protrusions 20 and voids 30. The diameter of the void depends upon the diameter (or width for non-uniform and/or non-cylindrical voids) of the one or more protrusions, plus the sidewall clearance. Each void 30 can have diameter of 40 to 2,000 microns, 50 to 500 microns, 65 to 300 microns, 75 to 200 microns, or 10 to 5000 microns, 50 to 5000 microns, 500 to 5000 microns, or 800 to 2,500 microns. Or, void 30 diameters may be even larger, such as up to 2.5 cm. The diameter of a void 30 may be constant, decreasing with increasing depth, or increasing with increasing depth. For example, the voids 30 can have a first diameter at a first depth and a second diameter at a second depth deeper than the first depth. The first diameter can be larger than the second diameter, i.e., inward taper. Or, the second diameter can be larger than the first diameter, i.e., outward taper.

The sidewalls of the voids 30 can be completely vertical, tapered, curved, or the sidewalls can include combinations thereof. In one embodiment, the voids 30 have tapered sidewalls. In one embodiment, sidewalls with an inward taper will typically have a degree of taper of 0° to 50°, 2° to 30°, or 5° to 25°. In another embodiment, the sidewalls of the voids comprise a combination of vertical and curved sidewalls.

Figure 14A:
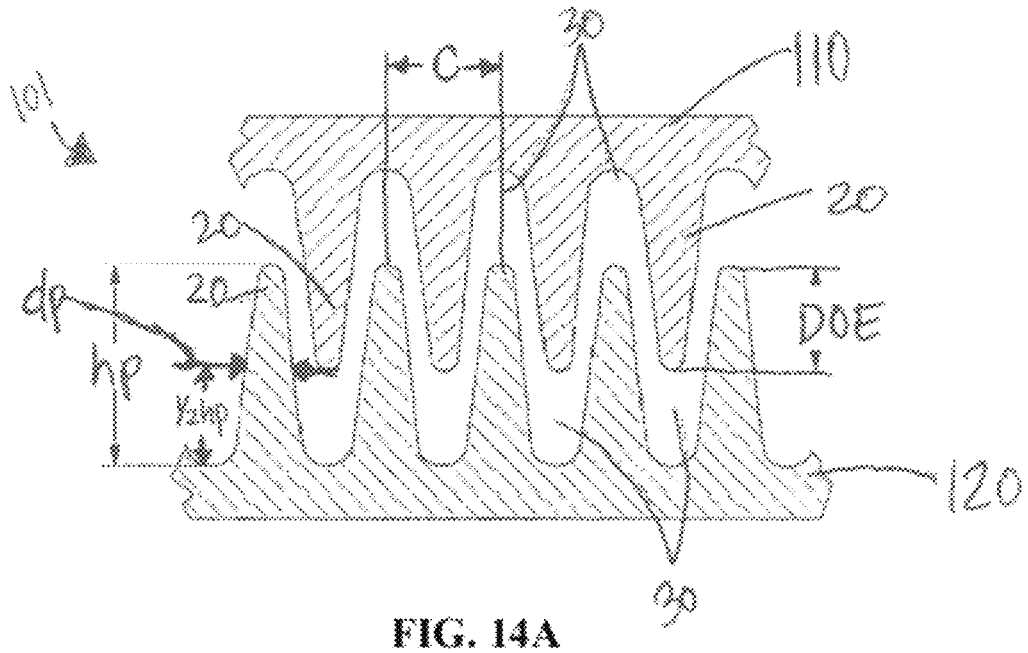
FIGS. 14A-D illustrate exemplary combinations of voids 30 and protrusions 20.
Figure 14B:
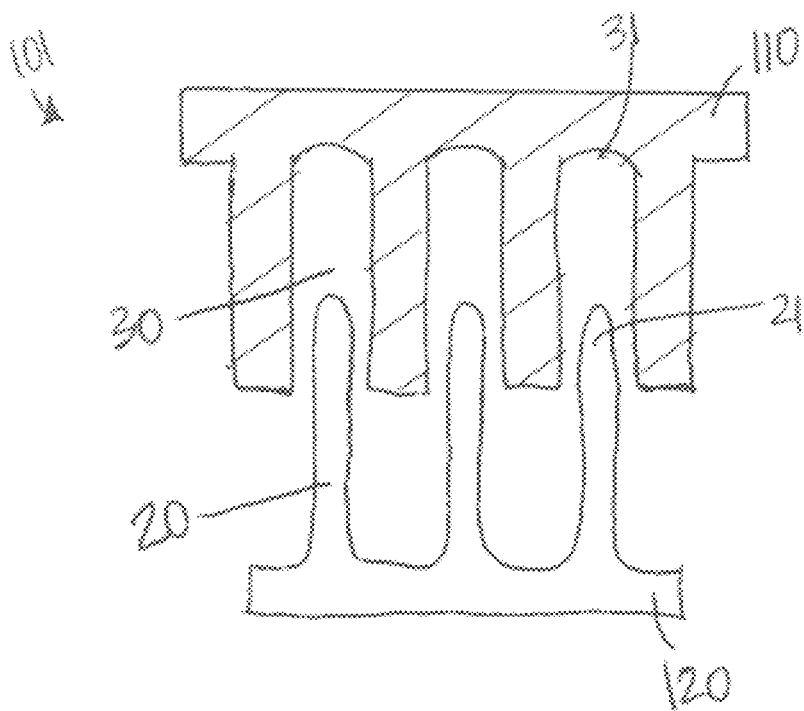
Figure 14C:
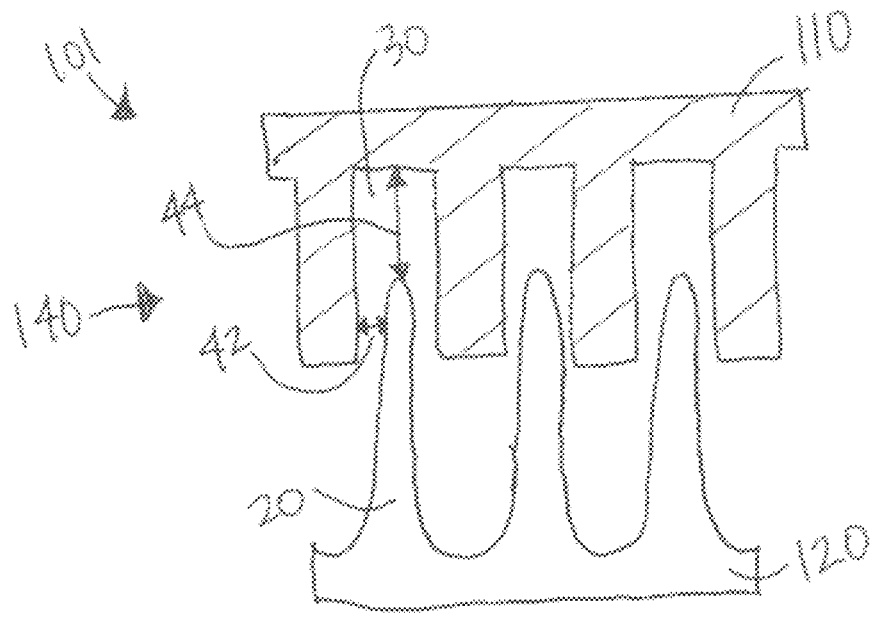
Figure 14D:
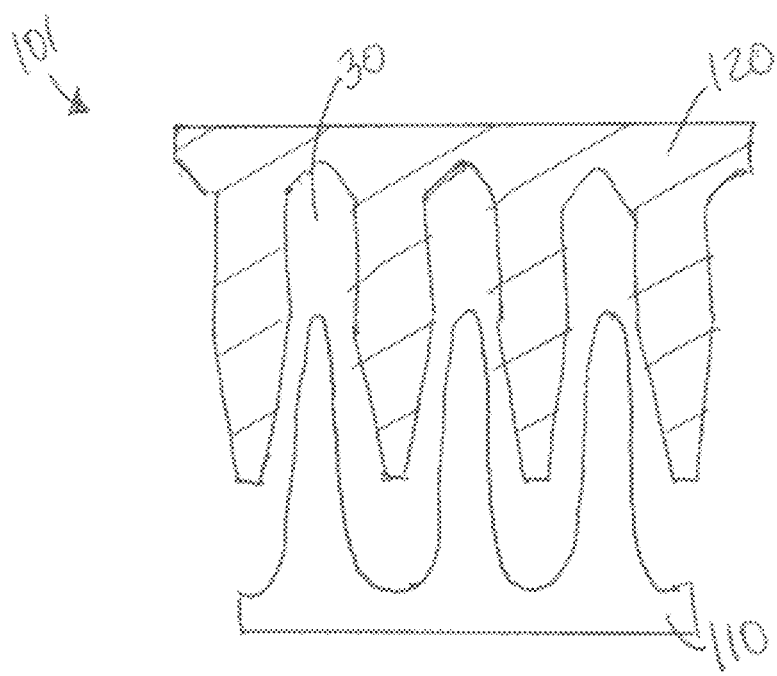
Figure 15A:
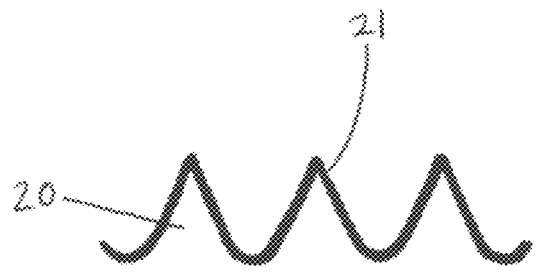
FIGS. 15A-H are illustrations of various protrusion geometries.
Figure 15B:
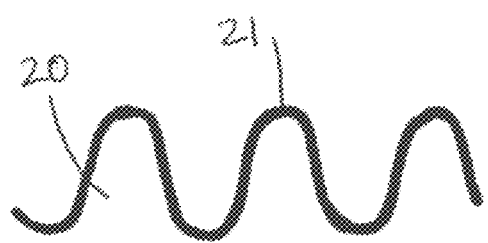
Figure 15C:
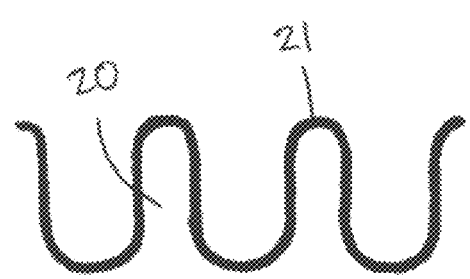
Figure 15D:
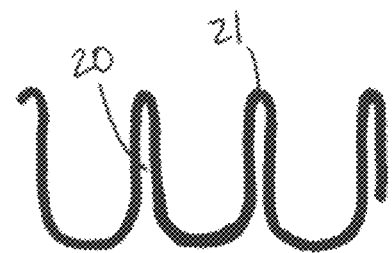
Figure 15E:
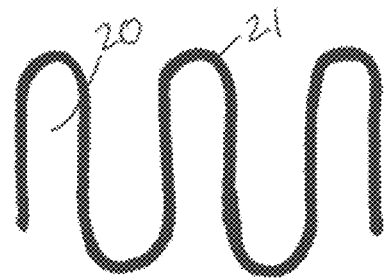
Figure 15F:
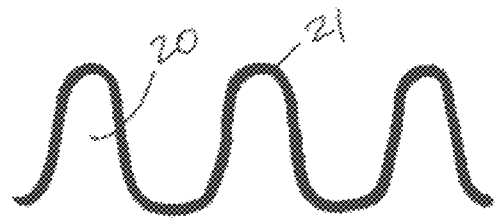
Figure 15G:
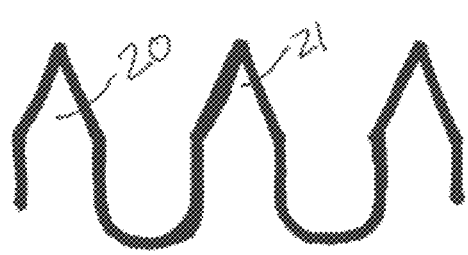
Figure 15H:
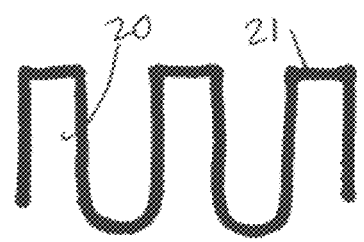

Protrusions 20 on one forming structure 110,120 can have varying heights or the substantially same height. The protrusions 20 can have heights of 100 microns to 2,000 microns, at least 500 microns, at least 700 microns, at least 900 microns, or at least 1,100 microns. Or, the protrusions 20 can have larger heights of up to 7.5 cm, 5 cm, 2.5 cm, up to 2 cm, up to 1.5 cm, up to 1 cm, up to 0.5 cm, or up to 0.1 cm. Preferably, the protrusions 20 have a height that is at least three times the total thickness of the webs. The protrusions 20 can have a diameter, which for a generally cylindrical structure is the outside diameter. For non-uniform cross-sections, and/or non-cylindrical structures of protrusions 20, diameter dp is measured as the average cross-sectional dimension of protrusions 20 at ½ the height hp of the protrusions 20, as shown in FIG. 14A. The protrusions 20 can have diameters dp of from 10 microns to 770 microns, 50 microns to 600 microns, 50 microns to 500 microns, 65 microns to 400 microns, or 75 microns to 300 microns. Or, the protrusions 20 can have larger diameters dp of up to 2.5 cm, up to 2 cm, up to 1.5 cm, up to 1 cm, up to 0.5 cm, up to 0.1 cm, or up to 0.08 cm.

Various protrusion shapes are shown in FIGS. 15A-H. The protrusions 20 of the forming structures 110,120 can have distal ends, or tips 21 that are flat, rounded or sharp, depending upon whether it is desired to produce a web 60 having three-dimensional elements ("3-D elements") 62 with distal ends 66 that are open, or apertured 67 (requiring a sharper protrusion on the forming structure 110) or closed 68 (requiring a more rounded protrusion on the forming structure 110). Less sharp or rounded protrusion tips 21 may lead to more side thinning of the sidewalls 70 of the 3-D elements 62 and even rupturing to form side openings, or apertures 71. In some embodiments, the tips 21 of the protrusions 20 of the forming structures 110,120 are rounded and have a certain tip radius, such as from 5 to 300 microns, from 10 to 150 microns, from 15 to 100 microns, from 20 to 75 microns, or from 30 to 60 microns.

The sidewalls of the protrusions 20 can be completely vertical, tapered, curved, or combinations thereof. Tapered sidewalls can also allow the web 60 to more easily separate from the forming structures 110,120 after forming. In one embodiment, the sidewalls will typically have a degree of taper of from 0° to 50°, from 2° to 30°, or from 5° to 25°. In other embodiments, the protrusions 20 can be spherical, ellipsoid, or snowman-shaped, having different or varying diameters along the height of the protrusion 20. In a preferred embodiment, protrusions 20 comprise tips 21 with a smaller radii and sidewalls with a steeper degree of taper.

Figure 16:
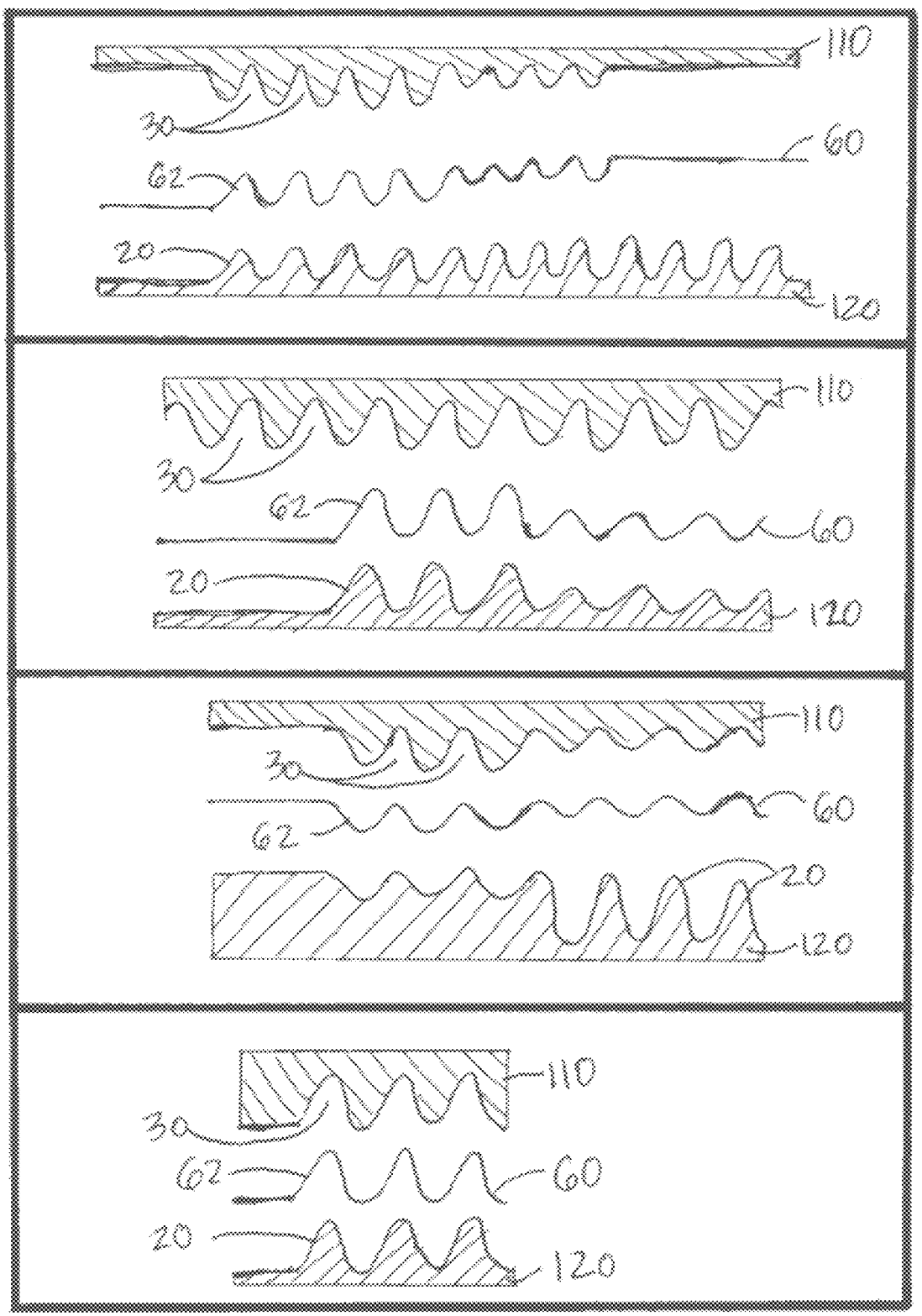
FIG. 16 is a representation of forming structures and a web with varying amplitudes.

Forming elements 10 of a single forming structure 110, 120 can have varying geometries, such as height of the protrusions 20 and depth of the voids 30, or combinations of both. For example, the forming elements 10 can gradually increase in height or over a range of tens or hundreds of adjacent protrusions 20, which can result in the web 60 having discrete 3-D elements 62 with varying heights. Other features of the forming structures 110,120 which result in corresponding features of the discrete 3-D elements 62 can be adjusted to form gradient characteristics in the discrete 3-D elements 62 of the web 60. As shown in FIG. 16, the forming structures 110,120 can include an area density gradient of forming elements 10.

Figure 17A:
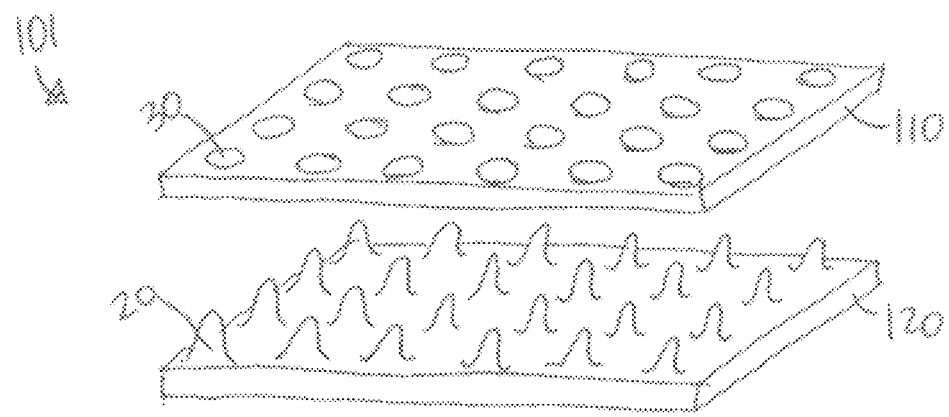
FIGS. 17A-C are illustrations of different ratios of protrusions to voids.
Figure 17B:
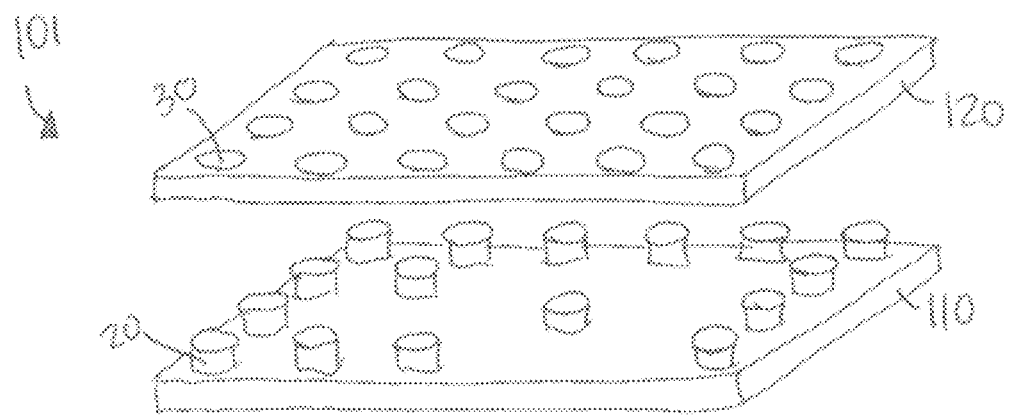
Figure 17C:
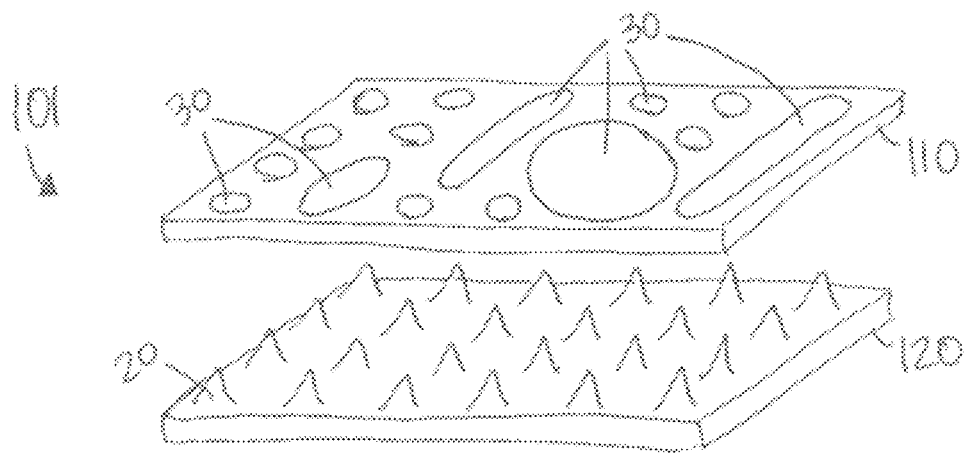

FIGS. 17A-C show various ratios of protrusions 20 to voids 30 on forming structures 110,120. In some embodiments, the protrusions 20 and voids 30 are sized relative to one another to allow mating to successfully produce a web 60 of the present invention. The ratio of protrusions 20 to voids 30 may be 1:1 so that each protrusion 20 has a corresponding void 30, such as shown in FIG. 17A. Or, the ratio of protrusions 20 to voids 30 may be less than 1:1, so that there are extra voids 30 which do not match up to protrusions 20, as shown in FIG. 17B. Extra voids 30 may simplify alignment of two mated forming structures. Or, the ratio of protrusions 20 to voids 30 may be greater than 1:1, for instance, two, three, four, or more protrusions 20 may be sized to mate with only one void 30, as shown in FIG. 17C. The ratio of protrusions 20 to voids 30 may range from at least about 1:1, at least about 100:1, at least about 10,000:1, or even more, such as when multiple discrete protrusions 22 mate with one continuous void 38, as shown in FIG. 8. In other embodiments, the protrusions 20 need not mate with voids 30, but can mate with the void 30 spaces between other protrusions 20. For example, FIGS. 11A and 11B show a pair of forming structures 101 wherein both forming structures 110,120 are rollers comprising protrusions 20, with the spaces between forming voids 30. In this embodiment, the protrusions 20 on each roller 108,109 are lined up so they engage.

In certain embodiments, the shapes of the protrusions 20 mimic the shapes of the voids 30. For instance, protrusions 20 and voids 30 may both be generally cylindrical and tapered and may have matching or different angles of taper. Or, in certain embodiments, the shapes of the protrusions 20 do not mimic the shapes of the voids 30. For example, protrusions 20 may be circular while voids 30 may be squared or oval. The forming elements 10 of the forming structures 110,120 can have a variety of different cross-sectional shapes, such as generally columnar or non-columnar shapes, including circular, oval, hour-glass shaped, star shaped, polygonal, and the like, and combinations thereof. Polygonal cross-sectional shapes include, but are not limited to, rectangular, triangular, hexagonal, or trapezoidal.

In general, the forming structures 110,120 for a given portion thereof will include at least about 200, at least about 220; from about 240 to about 10,000; from about 300 to about 5,000; or from about 350 to about 3,000 forming elements 10 per square centimeter. Or, the forming structures 110,120 for a given portion thereof will include at least about 0.1 to about 10,000; 4 to about 10,000; about 95 to about 10,000; about 240 to about 10,000; about 350 to about 10,000; about 500 to about 5,000; or about 700 to about 3,000 forming elements 10 per square centimeter. One objective of the present invention is that there is sufficient web tension and/or friction between the precursor web 50 and the forming structures 110,120 to allow the web 60 formation to occur. The web 50 is held in place during forming by web tension and/or friction in the machine direction, cross direction, angle from the machine direction, or combination thereof.

Referring to FIG. 10, adjacent protrusions 20 have a center-to-center spacing C which can be controlled so as to control the spacing of the resulting discrete 3-D elements 62. Center-to-center spacings among adjacent protrusions 20 may be the same or different. Acceptable center-to-center spacings are less than about 800 microns (i.e., micro) or greater than about 800 microns (i.e., macro). Other acceptable center-to-center spacings are from about 30 microns to about 700 microns, about 50 microns to about 600 microns, about 100 microns to about 500 microns, or about 150 microns to about 400 microns. Further acceptable center-to-center spacings are about 30 microns to about 32,000 microns, about 100 microns to about 5,000 microns, about 150 microns to about 1,000 microns, about 150 microns to about 600 microns, or about 180 microns to about 500 microns. In some embodiments, at least one protrusion 28 has center-to-center spacings of less than about 800 microns with at least three, at least four, or at least five of its adjacent protrusions 20. Or, at least 25%, at least 50%, at least 75%, at least 95%, or all of the protrusions 20 on a forming structure have center-to-center spacings of less than about 800 microns with at least three, at least four, or at least five of their adjacent protrusions 20. Or, at least one protrusion 28 has center-to-center spacings of greater than about 800 microns with at least three, at least four, or at least five of its adjacent protrusions 20. Or, at least 25%, at least 50%, at least 75%, at least 95%, or all of the protrusions 20 on a forming structure have center-to-center spacings of greater than about 800 microns with at least three, at least four, or at least five of their adjacent protrusions 20.

Forming elements 10 may be aligned in the machine direction, cross direction, or at an angle from the machine direction or cross direction. The forming elements 10 may be arranged in random arrays or non-random arrays. Examples of non-random arrays include rectangular, hexagonal, square, and combinations thereof. Arrays of forming elements 10 may be designed to increase the strength of the web 60, for example, by minimal alignment in the machine direction, the cross direction strength will be increased. Arrays of forming elements 10 may be designed to maximize ease of tearing the web 60, for example, with serrated or linear alignments.

In certain embodiments, a portion of the forming structures 110,120 can include area densities of forming elements 10 as described above, while other portions of the forming structures 110,120 may include no forming elements 10, as shown in FIG. 16. The areas of the forming structures 110,120 having no forming elements 10 can be located at a different radial distance or in a different horizontal plane. In other embodiments, the forming elements 10 of the forming structures 110,120 can be located at a different radial distance or in different horizontal planes of the forming structures 110,120. The portions having no forming elements 10 and/or the portions having forming elements 10 located in different horizontal planes of the forming structures 110,120 can be in the form of a specific pattern or design, such as a flower, bird, ribbon, wave, cartoon character, logo, and the like, so that the web 60 will have a portion that stands out visually from, and/or has a different hand feel when touched relative to, the remainder of the web. For example, the web 60 can include a non-formed portion that stands out visually from, and/or has a different hand feel from formed portions, such as described in U.S. Pat. No. 5,158,819. Portions of forming structures 110,120 having no forming elements 10 do not factor into the center-to-center spacing requirements of adjacent forming elements in portions of forming structures 110,120 having forming elements 10. For instance, if two portions with forming elements are separated by a third portion without forming elements, forming elements from the first portion are not considered adjacent to forming elements from the second portion; only forming elements within each portion are considered adjacent to one another.

Process for Making a Formed Web

One process for making a formed web includes a forming step in which a precursor web is moved through a deformation zone located between a pair of mated forming structures. The forming structures each comprise forming elements such as protrusions and voids. The resultant web includes a plurality of discrete three-dimensional elements ("3-D elements"). The process may also include an additional forming step in which the web is moved through at least one other deformation zone located between a second pair of mated forming structures. The resultant web includes a plurality of discrete 3-D elements imparted by the first forming step, as well as those elements imparted by the second forming step, thereby providing a complex web. The second discrete 3-D elements may extend from the first or second side of the web, may be in the same or similar location as the first 3-D elements, may be placed between the first 3-D elements to increase area density, or may be larger or smaller or the same size as the first 3-D elements, e.g., a web may be formed which has a micro-texture as well as a macro-texture.

A suitable process comprises at least one pair of mated forming structures 101. The forming structures may comprise rollers, plates, belts, sleeves, or the like, or combinations thereof. Suitable pairs of forming structures 101 include, but are not limited to: a pair of counter-rotating rollers that define a nip therebetween, a pair of plates, a pair of belts, or the like.

If the mated pair 101 of forming structures 110,120 both include protrusions 20 and voids 30, the discrete 3-D elements 62 can be formed in the web 60 extending from the surface of the web 60 opposite the surface from which the discrete 3-D elements 62 formed by the voids 30 of the forming structures 110,120 are formed. See, for example, FIGS. 11A and 11B. As a result, a two-sided web 60 can be created, having different patterns or dimensions of 3-D elements 62 on each side of the web 60. Depending upon the strain generated by the forming apparatus, as well as the geometric shapes of the voids 30 and optional pillars 24 of the forming structures 110,120, the discrete 3-D elements 62 of the web 60 can have open, or apertured, distal ends 67; closed distal ends 68; open, or apertured, sidewalls 71; closed sidewalls 72, or chads 73. In addition, the sizes, shapes, and area densities of the 3-D elements 62 on one side of the two-sided web 60 can be controlled independent of the other side of the two-sided web 60.

Figure 18:
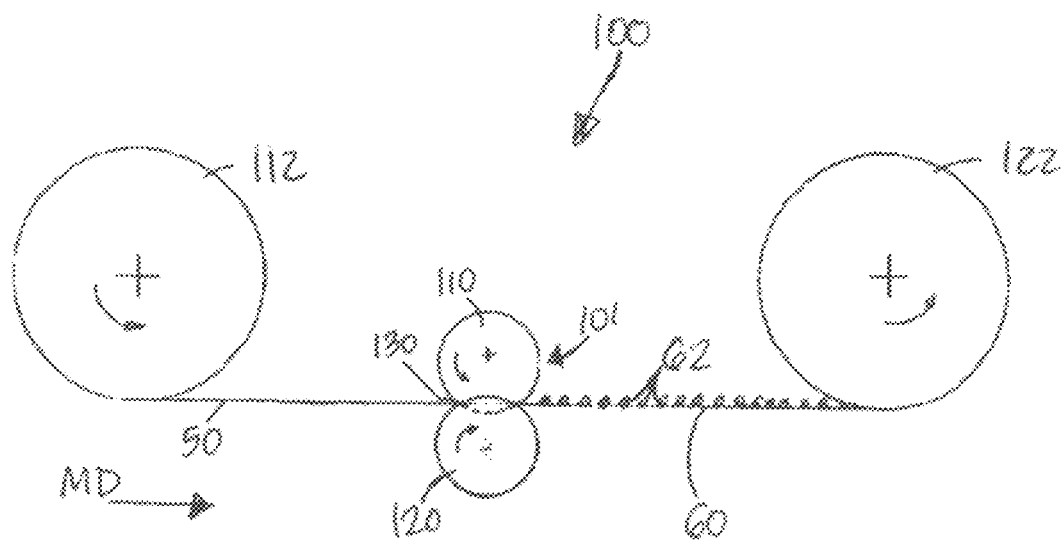
FIG. 18 is a perspective view of a forming process.

As shown in FIG. 18, a process 100 for forming a web 60 includes moving a precursor web 50 from a first supply roll 112 through a pair of mated forming structures 101 to a rewind roll 122. The pair of forming structures 101 comprises a first forming structure 110 and a second forming structure 120 which mate at a deformation zone 130. In a preferred embodiment, at least the first forming structure 110 comprises voids 30 and at least the second forming structure 120 comprises protrusions 20. The precursor web 50 is moved through the deformation zone 130 between the two forming structures wherein the protrusions on the second forming structure 120 mate, or engage, with the voids on the first forming structure. The forming structures 110,120 engage at an engagement position 140 and have a depth of engagement DOE wherein there is an acceptable sidewall clearance 42 and tip-to-valley clearance 44 between protrusions 20 and voids 30, for example, as shown in FIGS. 14A-D. At the engagement position 140, at least a majority of the engaged voids and protrusions are separated from each other by a sidewall clearance 42 ranging from about 30 microns to about 300 microns and a tip-to-valley clearance 44 of greater than 30 microns. Typically, the sidewall angle of the protrusions 20 are defined such that when the forming structures engage, there is sufficient clearance for the web and the web is not sheared (where portions of the web forced to slip relative to other portions) or pinched by the forming structures. The rolls 110,120 may rotate at substantially the same speed as the speed at which the web is fed through the nip between the rolls; or, they may rotate at a greater or lesser speed than the speed at which the web is fed through the nip between the rolls.

The forces in the deformation zone 130 upon the precursor web 50 are sufficient to cause the precursor web 50 to conform to the forming elements 10 to form a web 60 having discrete 3-D elements 62. The conformation of the precursor web 50 to the forming elements 10 can be partial, substantial, or complete conformation (unless rupture occurs), depending upon the web 50, the strain induced on the web 50, the temperature, and the topography of the forming structures 110,120.

Figure 19:
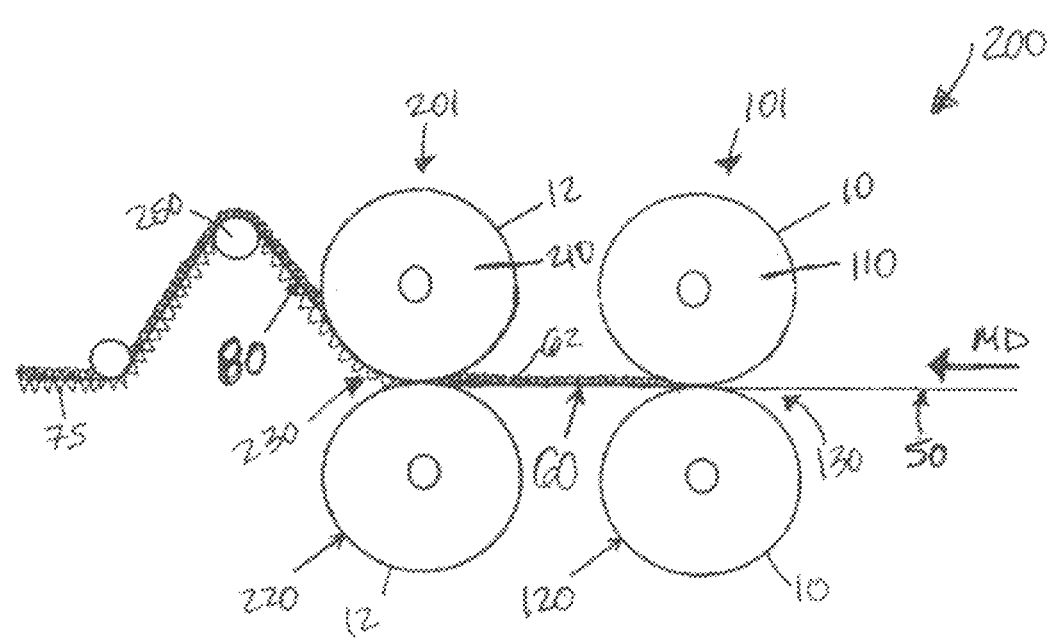
FIG. 19 is a perspective view of another forming process.

The process can optionally be combined with other processes to further manipulate the web 60. For example, as shown in FIG. 19, a web 60 may go through at least a second deformation zone 230 to form a second formed web 80. Additional webs may be introduced to the process at any time. The forces in the deformation zone 230 upon the first web 60 are sufficient to cause the first web 60 to conform to the second forming elements 12 to form a second formed web 80 having second discrete 3-D elements 74 and/or third 3-D elements 75 as well as the first discrete 3-D elements 62 (or some deformed variation of them). Third 3-D elements 75 shown in FIG. 7 were made according to US 2006/0087053 A1. The conformation of the first web 60 to the additional forming elements can be a partial, substantial, or complete conformation, depending upon the web 60, the strain induced on the web 60, the temperature, and the topography of the forming structures 210,220. A shadow effect of a pattern can be created using a first and second pair of forming structures 101,201 having aligned portions having no forming elements 10 and controlling the location of the first web 60.

Figure 20A:
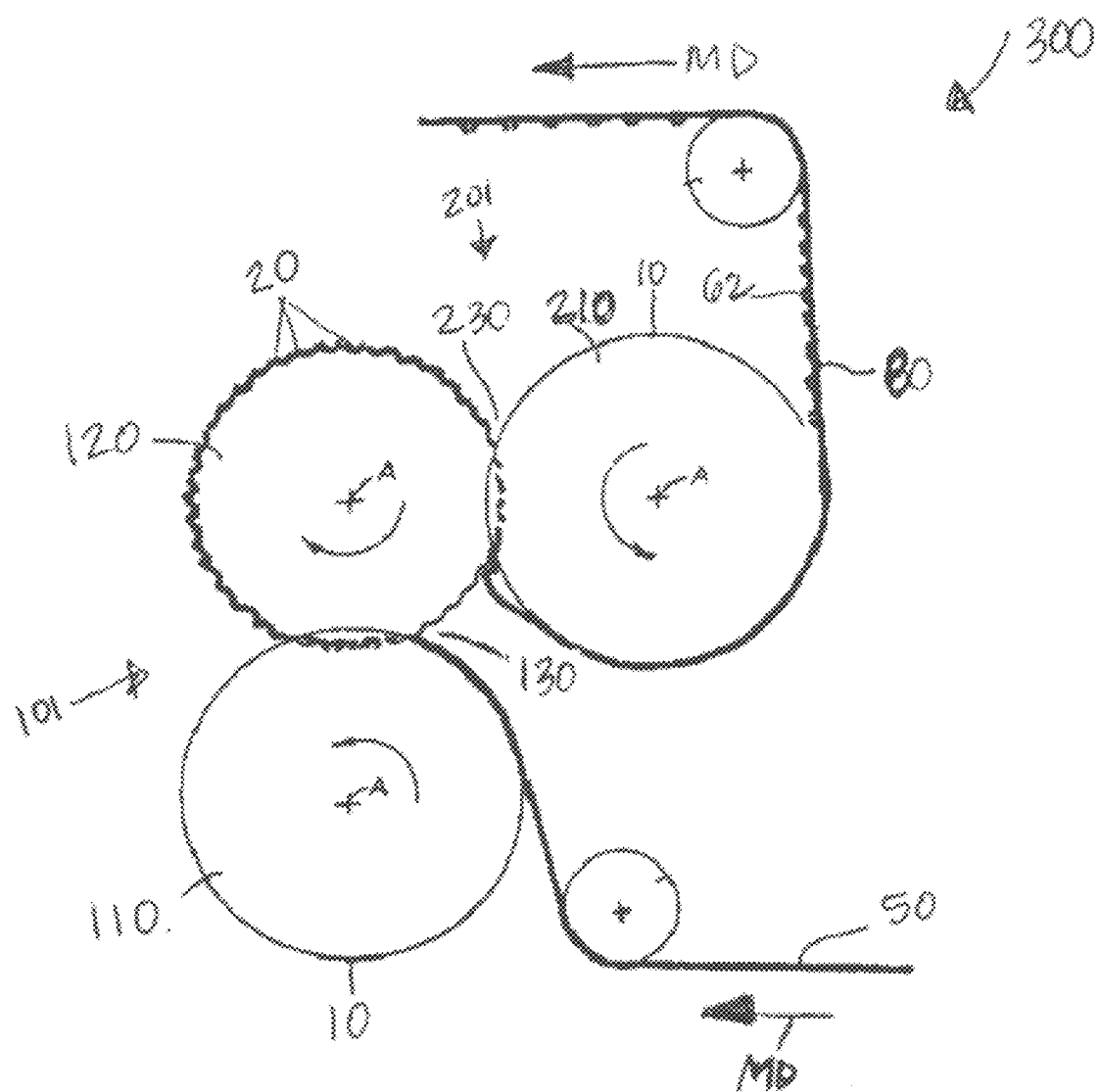
FIGS. 20A and 20B are perspective views of forming processes.
Figure 20B:
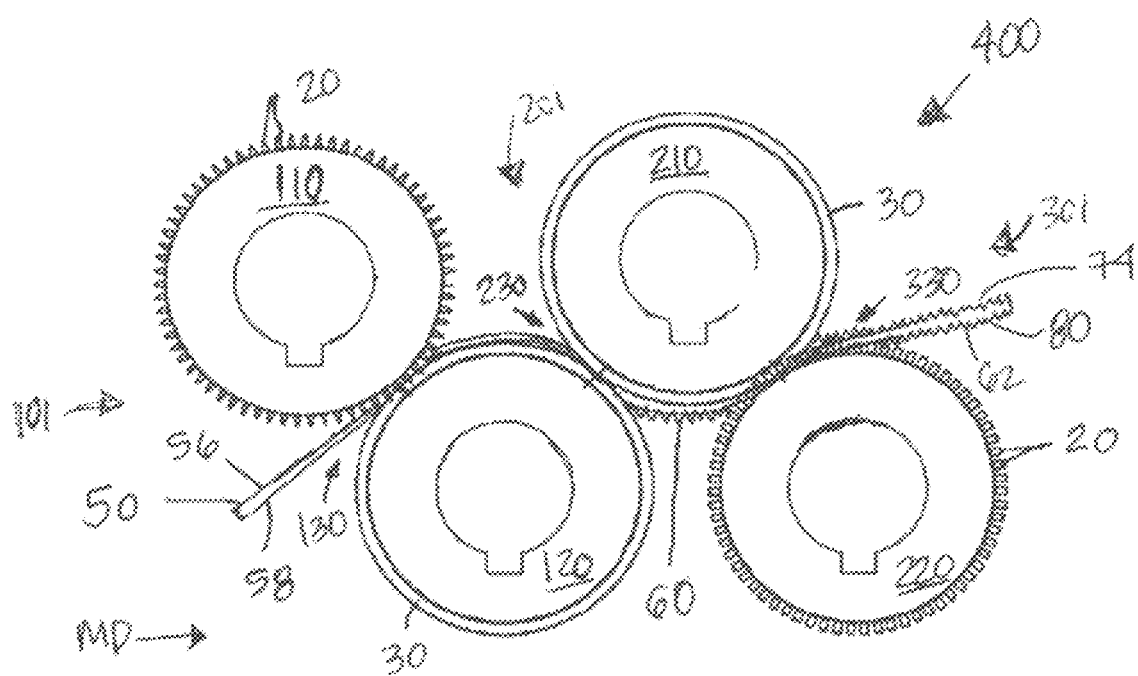

The second pair of mated forming structures 210,220 may comprise third and fourth forming structures separate from the first and second forming structures. As shown in FIG. 19, the two deformation zones, or nips, 130,230 are separated in space. Alternatively, a second deformation zone 230 can be created by a third forming structure 210 if it is nested with or mated to either of the first or second forming structures 110,120. For example, in the process 300 shown in FIG. 20A, forming structures 110,210 can be mated with forming structure 120 in a planetary arrangement. Forming structures 110,210 have at least some forming elements 10 in a similar size and/or array so as to mate with second forming structure 120. If the web 60 is still registered on the same forming structure/protrusions 20, as shown in FIG. 20A, the second deformation zone 230 may yield a greater degree of conformation of the web 60 to at least some of the forming elements 10 (everywhere or in certain locations). If the web 60 is not registered on the same forming structure/protrusions, as shown in the nested arrangement of FIG. 20B, the second deformation zone 230 or third deformation zone 330 may increase area density of the discrete 3-D elements with cheaper tooling and at faster line speeds as well as create a web 80 having 3-D elements extending from both sides of the web. For examples, see U.S. application Ser. No. 12/879,567 and U.S. patent application Ser. No. 13/094,206, "Method for Deforming a Web", to Orr filed on the same date as the present application.

While not being bound by theory, it is believed that factors such as the precursor web 50; the shape, size, variety, and center-to-center spacing of the protrusions 20 and voids 30; the strain induced on the precursor web 50; the temperature; and the topography of the forming structures 110,120; as well as the strain applied can be adjusted to produce a desired web 60 having, e.g., discrete 3-D elements 62 on one or both sides of the web 60, with closed or open distal ends 66 or closed or open sidewalls 70, etc. To obtain permanent deformation of the precursor web 50 and the first web 60 to form the first web 60 and the second web 80, respectively, the strain applied is generally sufficient to stretch the precursor beyond its yield point. Different levels of strain may be induced by varying the depth of engagement between the forming structures. In one embodiment, chads form at higher depths of engagement and/or higher temperatures.

When a micro-textured web is desired, the process disclosed herein allows for use of rigid forming structures having narrower center-to-center spacing between adjacent forming elements as well as a higher area density of forming elements to produce micro-textured webs having smaller scale spacing between adjacent discrete 3-D elements and a high density of discrete 3-D elements. Previously, rigid forming structures were designed to have fewer forming elements and wider spacing between adjacent elements because they were cheaper and easier to manufacture and had significantly increased life span as compared to forming structures having a higher area density of forming elements with narrower spacing between adjacent elements. Processes exist for making a micro-textured web using a compliant material, such as water, rubber, and air in conjunction with a rigid structure; however, up to this point, two rigid mated forming structures have not been able to create micro-textured webs with such small scale. It has been discovered that applying the forming structure techniques such as those disclosed in U.S. Pat. No. 7,655,176 to create both of the rigid, mated forming structures of the present invention can allow high speed innovative tooling for processes of the current invention. Now, it is possible to create small length scales of protrusions and voids on pairs of rigid mated forming structures.

The process can have relatively short dwell times. Dwell time refers to the amount of time strain is applied to a given portion of the precursor web 50 or the first web 60, usually the amount of time a given portion of the precursor web 50 or the first web 60 spends positioned in the deformation zone, or nip 130,230,330 between pairs of forming structures 101,201,301. Strain is typically applied to the precursor web 50 or the first web 60 for a dwell time of less than 5 seconds, less than 1 second, less than 0.5 second, less than 0.1 second, less than 0.01 second, or less than 0.005 second. For example, the dwell time can be 0.5 milliseconds to 50 milliseconds. Strain can be applied to the precursor web 50 during a first deformation zone 130 for a first dwell time and strain can be applied to the first web 60 during a second deformation zone 230 for a second dwell time. The first and second dwell times can be substantially equal or can be different. Even with such relatively short dwell times, webs can be produced with desirable structural features described herein. As a result, the process of the disclosure enables high speed production of webs. In other embodiments, the process can have relatively long dwell times, such as the method for incrementally stretching a web, described in US 2008/0224351.

The precursor web 50 or the first web 60 can be fed between the first and second forming steps at a rate of at least 0.01 meters per second, at least 1 meter per second, at least 5 meters per second, or at least 10 meters per second. Other suitable rates include, for example, at least 0.01, 0.05, 0.1, 0.5, 1, 2, 3, 4, 5, 6, 7, 8, 9, or 10 meters per second. The rate at which the precursor web 50 is fed between the first pair of forming structures 101 can be substantially the same or different as the rate the first web 60 is fed between the second pair of forming structures 201.

Any or each of the forming steps of the process can be carried out at ambient temperature, meaning that no heat is intentionally applied to the forming structures and/or webs. It should be recognized, however, that heat can be generated due to the high strain of the precursor web 50. As a result, the forming structures may be cooled in order to maintain the process conditions at the desired temperature, such as ambient temperature. Any or each of the forming steps of the process can also be carried out with the web having an elevated temperature. For example, the temperature of the web can be less than the melting point of the precursor web 50. For example, the temperature of the web can be at least 10° C. below the melting point of the precursor web 50. In general, the process can be carried out at a temperature of from 10° C. to 200° C., from 10° C. to 120° C., from 10° C. to 80° C., or from 10° C. to 40° C. The web 50 can be heated by a preheating step or by actively heating one or both of the forming structures. The temperature can be measured by, for example, a non-contact thermometer, such as an infrared thermometer or a laser thermometer, measuring the temperature at the deformation zone 130,230. The temperature can also be determined using temperature sensitive material such as Thermolabel available from Paper Thermometer Company.

Uses of Formed Web

Formed webs of the present invention can be utilized in a number of different ways, such as component materials of absorbent articles (such as topsheets, backsheets or release paper wrappers, e.g., for a feminine hygiene article, diaper, or adult incontinence article), packaging (such as flow wrap, shrink wrap, or polybags), trash bags, food wrap, wipes, electronic components, wall paper, clothing, window coverings, placemats, book covers, and the like.

EXAMPLES

Example 1

A formed web 60 may be produced using flat plate forming structures 110,120. The first forming structure 110 includes parallel continuous grooves 39 and parallel ridges 28 running in a first direction, with a center-to-center spacing of about 520 microns in a second direction. The ridges 28 have a taper angle of about 5 degrees from vertical. The grooves 39 have a depth of about 940 microns and a diameter at half-depth of about 320 microns. The second forming structure 120 includes about 320 teeth 26 per square centimeter, the teeth 26 having a general shape as shown in FIGS. 21A-C. The teeth 26 are arranged in a rectangular array, with a center-to-center spacing of about 610 microns in a first direction and about 520 microns in a second direction. The teeth 26 have straight, vertical sidewalls in the first direction and tapered inward at an angle of about 10 degrees in the second direction. The teeth 26 have a height of about 610 microns in the first direction, about 800 microns in the second direction, and a rectangular cross section with a first diameter of about 230 microns and a second diameter of 130 microns at half-height. The tips are rounded with a first radius of about 115 microns and a second radius of about 50 microns. The forming structures 110,120 are made from aluminum by EDM wire engraving. The precursor web 50 utilized is a polyethylene film having a fine square embossed pattern, obtained from the RKW-Group, Germany, that is about 18 microns thick and has a basis weight of about 17 grams per square meter (gsm).

The forming process is performed using a high speed research press (HSRP) at room temperature. The HSRP (described in detail in U.S. 2009/0120308) is designed to simulate a continuous production line process for embossing the precursor web 50. The HSRP is operated to simulate forming structure 110,120 roll diameters of 206 mm. The precursor web 50 is fed between the forming structures 110,120 in a pre-strained state of 1.5% in a first direction (parallel with the grooves and ridges) at a simulated rate of about 6 m/sec. The engagement is about 600 microns, at which point the sidewall clearances are about 105 microns in the second direction and the tip to valley clearance is about 330 microns.

Figure 22:
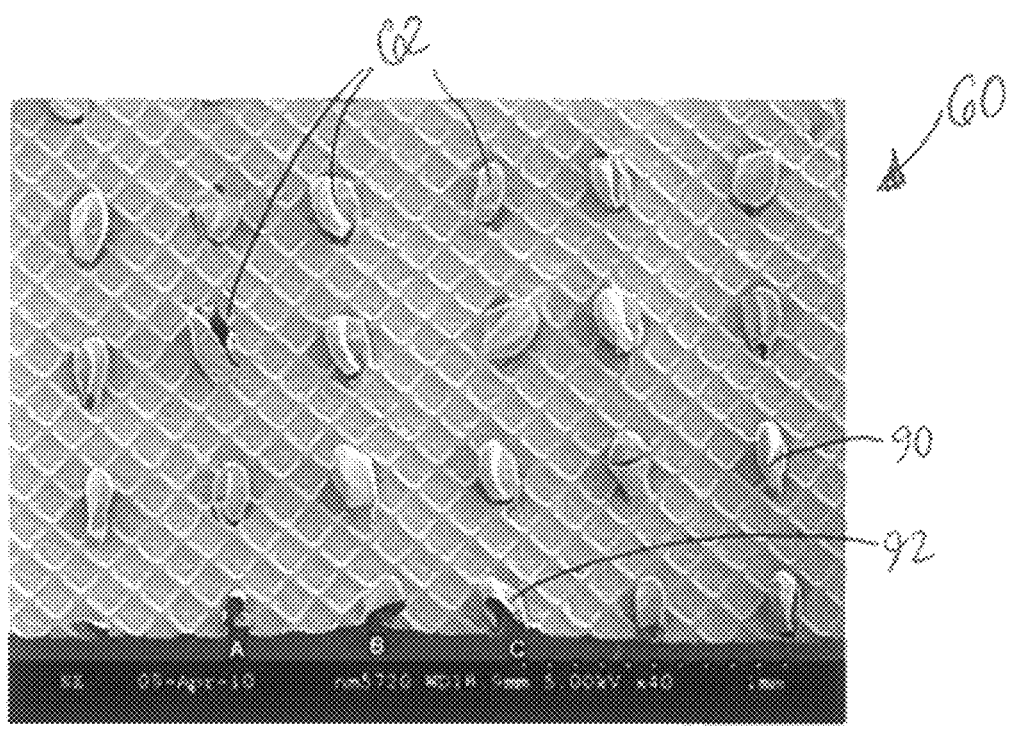
FIG. 22 illustrates the web of Example 1.

FIG. 22 is a SEM image which illustrates a resultant web 60 which includes a plurality of discrete 3-D elements 62. The fine square embossed pattern of the precursor web is still apparent. The discrete 3-D elements 62 are predominantly in the form of bubbles 90 and some hoods 92 with significant sidewall and tip thinning. Heights of the discrete 3-D elements 62 are about 165 microns with a first diameter at half-height of about 220 microns and a second diameter at half-height of about 108 microns.

Example 2

A formed web 60 may be produced on an apparatus similar to that shown in FIG. 8 using cylindrical forming structures 102,103. Both forming structures have an outer diameter of 145 mm and a width of 189 mm. The first forming structure 102 includes parallel continuous grooves 39 and parallel ridges 28 running in a first direction, with center-to-center spacing of about 508 microns in a second direction. The ridges 28 have a taper angle of about 4.4 degrees from vertical. The grooves 39 have a depth of about 1,000 microns and a diameter at half depth of about 340 microns. The second forming structure 120 includes about 287 teeth 26 per square centimeter, with a general shape as shown in FIG. 21A. The teeth 26 are arranged in a rectangular array, with a center-to-center spacing of about 685 microns in a first direction and about 508 microns in a second direction. The teeth 26 have straight, vertical sidewalls in the first direction and tapered inward at an angle of about 4.4 degrees from vertical in the second direction. The teeth 26 have a height of about 1,000 microns and a rectangular cross-section with a first diameter (length) of about 305 microns and a second diameter (width) of about 170 microns at half-height. The tips are rounded with a first radius of about 150 microns and a second radius of about 50 microns. Forming structures 102,103 are machined from aluminum to create grooves; then, forming structure 103 is EDM wire engraved to create teeth 26. The precursor web 50 utilized is a polyethylene film, obtained from Clopay Cincinnati, that is about 25 microns thick and has a basis weight of about 25 grams per square meter (gsm).

The forming process is performed by feeding the precursor web 50 into the nip 130 of the forming structures 102,103 at a line speed of 8 m/s at room temperature. The precursor web 50 is fed between the forming structures 102,103 in the machine direction (parallel with the grooves 39 and ridges 28). The web tension on the infeed side is about 1% to 5%, i.e., within the linear elastic region of the web. The web tension on the outfeed side should be greater than the infeed tension to keep the web moving. The outfeed wrap angle is 90°. The stripping idler roll 250 is positioned 0.8 mm away from the forming roll 103. The engagement is about 800 microns, at which point the sidewall clearances are about 95 microns in the second direction and the tip to valley clearance is about 200 microns.

Figure 23:
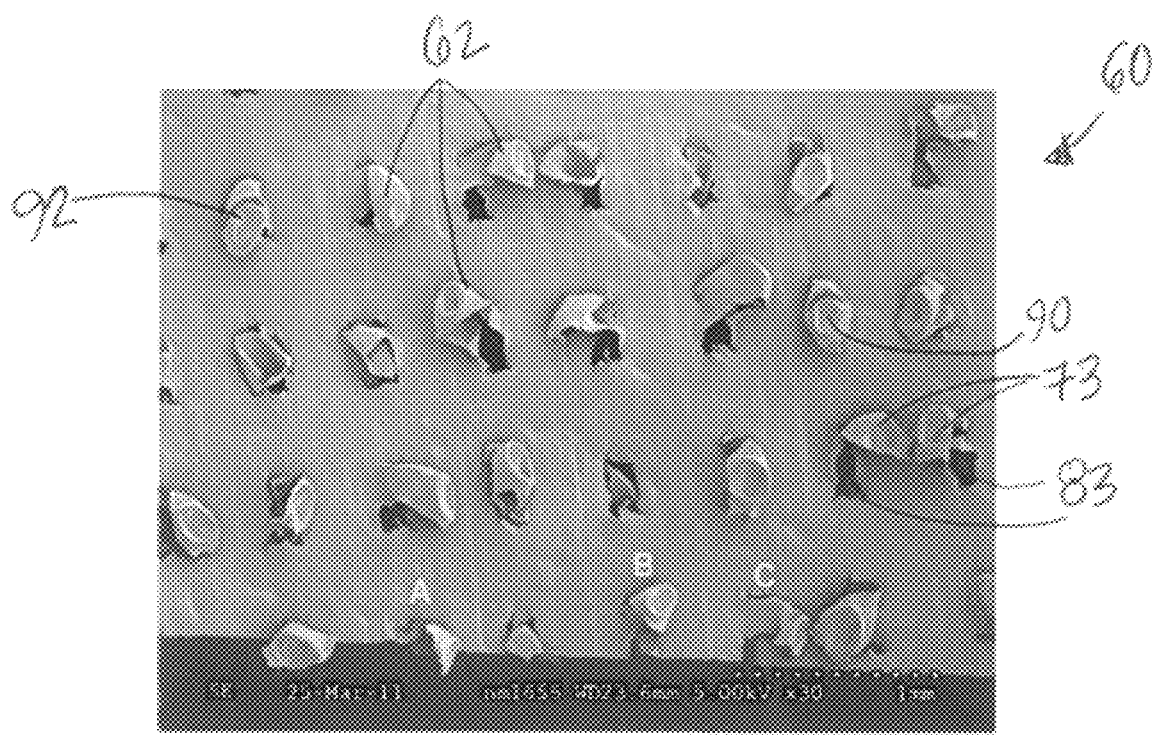
FIG. 23 illustrates the web of Example 2.

FIG. 23 is a SEM image which illustrates a resultant web 60 which includes a plurality of discrete 3-D elements 62. The 3-D elements 62 are in the form of bubbles 90, hoods 92, and chads 73 with significant sidewall and tip thinning.

Example 3

Figure 24:
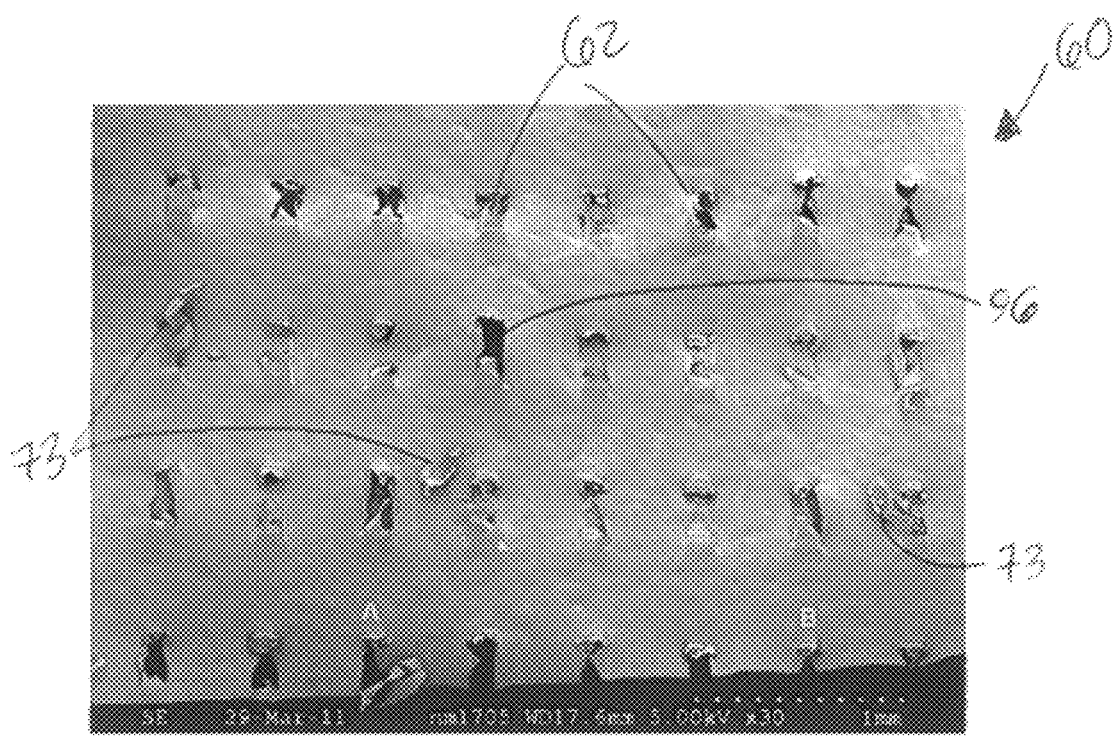
FIG. 24 illustrates the web of Example 3.

This Example is the same as Example 4, except that both forming structures 102,103 are maintained at 70 degrees Celsius during the process rather than room temperature. FIG. 24 is a SEM image which illustrates a resultant web 60 which includes a plurality of discrete 3-D elements 62. The discrete 3-D elements 62 are predominantly in the form of craters 96 and some chads 73 with significant sidewall and tip thinning.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising a body contacting-surface and a non-body contacting-surface, and a formed web comprising discrete three-dimensional elements formed therein, wherein at least some of the discrete three-dimensional elements comprise chads with corresponding apertures, wherein each corresponding aperture comprises two or less chads, wherein the discrete three-dimensional elements comprising chads form a portion of the body contacting-surface and at least a portion of each of the chads extends away from the non-body contacting-surface, and wherein each of the chads is attached along a portion of an aperture perimeter of the corresponding apertures, each of which forms a connection segment, wherein each connection segment is less than about 40% of the entire aperture perimeter, and wherein the formed web comprises a film, and wherein the formed web comprises land area surrounding the discrete three-dimensional elements comprising chads, and wherein each of the chads comprises at least a portion which is thinned at least about 25% relative to the thickness of the surrounding land area, wherein each of the chads comprises a length measured from the connection segment to a distal end which is greater than the diameter of the corresponding apertures, and wherein the formed web has a thickness between 5 and 150 microns.

2. The absorbent article of claim 1, wherein each of the chads are hingeable about the connection segment.

3. The absorbent article of claim 1, wherein the length is at least about 30 microns.

4. The absorbent article of claim 1, wherein the length is at least about 300 microns.

5. The absorbent article of claim 1, wherein each of the chads are bendable at various points along their length.

6. The absorbent article of claim 1, wherein the formed web comprises at least a second web in addition to the formed web, wherein an embossed seal joins at least a portion of the at least two webs, the seal including co-registered concentric discrete three-dimensional elements formed in the at least two webs, the discrete three-dimensional elements having open proximal ends.

7. The absorbent article of claim 1, wherein the three-dimensional elements comprising chads comprise a center-to-center spacing between adjacent three-dimensional elements comprising chads of about 100 microns to about 800 microns.

8. The absorbent article of claim 1, wherein the area density of the web is between about 0.1 to about 10,000 three-dimensional elements comprising chads per square centimeter.

9. The absorbent article of claim 1, wherein some but not all of the discrete three-dimensional elements comprise chads and corresponding apertures.

10. The absorbent article of claim 1, wherein the formed web comprises at least a second type of discrete three-dimensional elements.

11. The absorbent article of claim 10, wherein the formed web comprises at least a third type of discrete three-dimensional elements.

12. The absorbent article of claim 1, wherein each of the discrete three-dimensional elements comprising chads has only one chad per corresponding aperture.

13. An absorbent article comprising a body contacting-surface and a non-body contacting-surface, and a formed web, the formed web comprising generally planar first and second surfaces, the second surface being opposite the first surface, the formed web further comprising discrete three-dimensional elements extending from the first surface, wherein at least some of the discrete three-dimensional elements comprise chads with corresponding apertures, wherein each corresponding aperture comprises two or less chads, wherein the discrete three-dimensional elements comprising chads form a portion of the body contacting-surface and at least a portion of each of the chads extends away from the non-body contacting-surface, and wherein each of the chads is attached along a portion of an aperture perimeter of the corresponding apertures, each of which forms a connection segment, wherein each connection segment is less than about 40% of the entire aperture perimeter, wherein each of the chads is hingeable about the connection segment, wherein the formed web comprises a film, and wherein the formed web comprises land area surrounding the discrete three-dimensional elements comprising chads, and wherein each of the chads comprises at least a portion which is thinned at least about 25% relative to the thickness of the surrounding land area, wherein each of the chads comprises a length measured from the connection segment to a distal end which is greater than the diameter of the corresponding apertures, and wherein the formed web has a thickness between 5 and 150 microns.

14. The absorbent article of claim 13, wherein the absorbent article is a feminine hygiene article, adult incontinence article, or diaper.

15. The absorbent article of claim 13, wherein some but not all of the discrete three-dimensional elements comprise chads and corresponding apertures.

16. The absorbent article of claim 13, wherein the formed web comprises at least a second type of discrete three-dimensional elements.

17. The absorbent article of claim 16, wherein the formed web comprises at least a third type of discrete three-dimensional elements.

18. The absorbent article of claim 13, wherein the discrete three-dimensional elements comprising chads with corresponding apertures have only one chad per aperture.

19. An absorbent article comprising a formed web, wherein the web comprises a first surface and a second surface, wherein the first surface is a body contacting-surface and the second surface is a non-body contacting-surface, wherein the formed web comprises a plurality of chads with corresponding apertures, wherein each corresponding aperture comprises two or less chads, wherein each of the plurality of chads forms a portion of the body contacting-surface and at least a portion of each of the plurality of chads extends away from the non-body contacting-surface, and wherein each of the plurality of chads is attached along a portion of an aperture perimeter of the corresponding apertures, each of which forms a connection segment, wherein each connection segment is less than about 40% of the entire aperture perimeter, wherein the web additionally comprises at least second discrete three-dimensional elements, wherein the second discrete three-dimensional elements extend away from the body contacting surface, wherein the web additionally comprises at least third discrete three-dimensional elements, wherein the third discrete three-dimensional elements extend away from the body contacting surface, wherein the chads, second, and third discrete three-dimensional elements are different from each other in size and shape, and wherein the formed web comprises land areas surrounding the chads, wherein each of the plurality of chads comprises at least a portion which is thinned at least about 25% relative to the thickness of the surrounding land area, wherein each of the chads comprises a length measured from the connection segment to a distal end which is greater than the diameter of the corresponding apertures, and wherein the formed web has a thickness between 5 and 150 microns.

20. The absorbent article of claim 19, wherein the first, second, and third discrete three-dimensional elements are located in three different regions of the absorbent article.

21. The absorbent article of claim 19, wherein each corresponding aperture with chads comprises only one chad per aperture.

* * * * *